United States Patent
Quesniaux Ryffel et al.

(10) Patent No.: US 8,846,880 B2
(45) Date of Patent: Sep. 30, 2014

(54) **SYNTHETIC ANALOGUES OF PHOSPHATIDYL-*MYO*-INOSITOL MANNOSIDES WITH AN INHIBITORY ACTIVITY OF THE INFLAMMATORY RESPONSE**

(75) Inventors: Valérie Quesniaux Ryffel, Saint-Denis-En-Val (FR); Olivier Martin, Saint-Hilaire-Saint-Mesmin (FR); Sophie Front, Saint-Denis-En-Val (FR)

(73) Assignees: Centre National de la Recherche Scientifique—CNRS—, Paris (FR); Universite d'Orleans, Orleans (FR)

( * ) Notice: Subject to any disclaimer, the term of this patent is extended or adjusted under 35 U.S.C. 154(b) by 867 days.

(21) Appl. No.: 12/994,059

(22) PCT Filed: May 20, 2009

(86) PCT No.: PCT/FR2009/000595
§ 371 (c)(1),
(2), (4) Date: Jun. 1, 2011

(87) PCT Pub. No.: WO2009/153434
PCT Pub. Date: Dec. 23, 2009

(65) Prior Publication Data
US 2011/0224162 A1 Sep. 15, 2011

(30) Foreign Application Priority Data
May 23, 2008 (FR) ...................................... 08 53357

(51) Int. Cl.
*C07H 15/00* (2006.01)
*C07H 21/00* (2006.01)
*C07H 15/207* (2006.01)

(52) U.S. Cl.
CPC .................................. *C07H 15/207* (2013.01)
USPC .............................. 536/1.11; 558/70; 554/78

(58) Field of Classification Search
CPC ...................................................... C07C 39/00
USPC .............................. 536/1.11; 558/70; 554/78
See application file for complete search history.

(56) References Cited

U.S. PATENT DOCUMENTS
2004/0097465 A1    5/2004  Asari et al.

FOREIGN PATENT DOCUMENTS

| EP | 0 241 376 A1 | 10/1987 |
|----|--------------|---------|
| FR | 2 908 658 A  | 5/2008  |
| WO | WO 03/011336 A2 | 2/2003 |
| WO | WO 2005/049631 A1 | 6/2005 |
| WO | WO 2008/075983 A2 | 6/2008 |

OTHER PUBLICATIONS

Ainge, G. D. et al., "Phosphatidylinositol mannosides: Synthesis and adjuvant properties of phosphatidylinositol di- and tetramannosides", Bioorganic & Medicinal Chemistry, Elsevier Science Ltd, GB, vol. 14, No. 22, Oct. 30, 2006, pp. 7615-7624.
Ainge, G. D. et al., "Phosphatidylinositol mannosides: Synthesis and suppression of allergic airway disease", Bioorganic & Medicinal Chemistry Elsevier Science Ltd, GB, vol. 14, No. 16, Aug. 15, 2006.
Nigou J. et al., "Mannosylated Lipoarabinomannans Inhibit IL-12 Production by Human Dendritic Cells: Evidence for a Negative Signal Delivered Through the Mannose Receptor[1]", Journal of Immunology, American Association of Immunologists, US, vol. 166, No. 12, Jun. 15, 2001, pp. 7477-7485.
Ainge G. D. et al., "Phosphatidylinositol Mannoside Ether Analogues: Syntheses and Interleukin-12-Inducing Properties", J. Org. Chem., vol. 72, 2007, pp. 5291-5296.
Dyer, B. S. et al., "Synthesis and Structure of Phosphatidylinositol Dimannoside", J. Org. Chem., vol. 72, 2007, pp. 3282-3288.
Watanabe, Y. et al., "Regiospecific Synthesis of 2,6-Di-O-(α-D-mannopyranosyl)phosphatidyl-D-myo-inositol", J. Org. Chem., vol. 61, 1996, pp. 14-15.
Liu, X et al., "Total Synthesis of Phosphatidylinositol Mannosides of Mycobacterium tuberculosis", J. Am. Chem. Soc., vol. 128, 2006, pp. 3638-3648.
Cottaz, S. et al., "Parasite glycoconjugates. Part 3. Synthesis of substrate analogues of early intermediates in the biosynthetic pathway of glycosylphosphatidylinositol membrane anchors", Journal of the chemical society, Perkin Transactions 1, Chemical Society Letchworth, GB, No. 13, Jan. 1, 1995, pp. 1673-1676.
Stadelmaier, A et al., Synthesis of Serine-Linked Phosphatidylinositol Mannosides (PIMs), European Journal of Organic Chemistry, Wiley-VCH Verlag, Weinheim, DE, No. 15, Jan. 1, 2004, pp. 3292-3303.
Stadelmaier, a et al., Synthesis of phosphatidylinositol mannosides (PIMs), Carbohydrate Research, Elsevier Scientific Publishing Company. Amsterdam, NL, vol. 338, No. 23, Nov. 14, 2003, pp. 2557-2569.
Elie, C. J. J. et al. "Synthesis of 1-0-(1,2-Di-0-palmitoyl-SN-glycero-3-phosphoryl)-2-0-α-D-mannopyranosyl-D-MYO-Inositol: A Fragment of Mycobacterial phospholipids", Tetrahedron, Elsevier Science Publishers, Amsterdam, NL, vol. 45, No. 11, Jan. 1, 1989, pp. 3477-3486.

*Primary Examiner* — Patrick Lewis
*Assistant Examiner* — Everett White
(74) *Attorney, Agent, or Firm* — Arent Fox LLP

(57) ABSTRACT

The present invention relates to novel synthetic analogs of phosphatidyl-myo-inositol mannosides (hereinafter referred to as PIMs) of general formula (I): or a pharmaceutically acceptable salt thereof, to the method for preparing same and to the use thereof in the prevention or treatment of a disease associated with the overexpression of cytokines or of chemokines, in particular of TNF and/or of IL-12. The invention also relates to a pharmaceutical composition comprising at least one synthetic derivative of PIM.

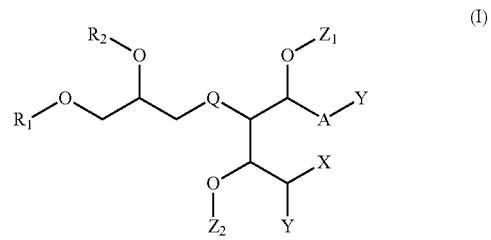

7 Claims, 13 Drawing Sheets

SYNTHETIC ANALOGUES OF PHOSPHATIDYL-*MYO*-INOSITOL MANNOSIDES WITH AN INHIBITORY ACTIVITY OF THE INFLAMMATORY RESPONSE

CROSS-REFERENCE TO RELATED APPLICATION

This application is a National Stage entry of International Application No, PCT/FR2009/000595, filed May 20, 2009, which claims priority to French Patent Application No. 08/53357 filed May 23, 2008, the disclosure of the prior application is incorporated in its entirety by reference.

TECHNICAL FIELD

The present invention relates to novel synthetic derivatives of phosphatidyl-myo-inositol mannosides (hereinafter referred to as PIMs), to the method for preparing same and to the use thereof in the prevention or treatment of a disease associated with the overexpression of cytokines or of chemokines, in particular of TNF and/or of IL-12.

The invention also relates to a pharmaceutical composition comprising at least one synthetic derivative of PIM.

In the description below, the references between square brackets [ ] refer back to the list of references provided at the end of the text.

PRIOR ART

The inhibition of the expression of pro-inflammatory cytokines such as TNF and interleukin 12 (hereinafter referred to as IL-12) p40 involved in many inflammatory responses constitutes a real medical need. The indications related to the expression of the cytokines include inflammatory, allergic and autoimmune diseases, including rheumatoid arthritis, Crohn's disease, multiple sclerosis, psoriasis, diabetes mellitus, lupus erythematosus, septic shock and chronic and acute pulmonary inflammations.

The molecules conventionally used in these indications are steroids. Several TNF-blocking agents (antibodies or soluble receptors) have been marketed since 2000. Four classes of molecules for inhibiting IL-12 secretion, including antibodies, are the subject of a patent/patent application [1].

However, steroids have side effects which limit the use thereof. Monoclonal antibodies or soluble receptors are expensive proteins requiring subcutaneous injections. In addition, these antibodies can have undesirable effects on resistance to infections, as has been shown for anti-TNF antibodies which can induce the reactivation of latent tuberculosis. Hyaluronan, described as an inhibitor of IL-12 production, has a very high molecular weight and is barely defined from a molecular point of view and difficult to synthesize [2].

There therefore remains a real medical need to find new inhibitors of pro-inflammatory cytokines such as TNF and IL-12 which overcome these faults.

Phosphatidyl-myo-inositol mannosides (hereinafter referred to as PIMs) are precursors of complex lipoglycans such as, for example, lipoarabinomannans (LAMs) and lipomannans (LMs), extracted from the walls of *mycobacteria*. Depending on their structure, PIMs can have different immunomodulatory activities.

PILAMs, originating from a fast-growing avirulent species such as *M. smegmatis*, are pro-inflammatory molecules which stimulate the production of TNF and of IL-12. On the other hand, LAMs capped with mannosyl residues (ManLAMs), originating from slow-growing *mycobacteria* such as *M. tuberculosis* and *M. bovis* BCG, are anti-inflammatory molecules capable of inhibiting the production of IL-12 and of TNF and of increasing the production of IL-10 by dentritic cells or by monocyte lines [8].

PILAMs stimulate macrophages by means of Toll-like receptors (TLR)-2, which are receptors that are involved in innate immunity, by stimulating the NF-kB signaling pathway [9]. The anti-inflammatory effects of ManLAMs have been attributed to the binding thereof to mannose receptors [10] or to DC-SIGN [11].

LMs, which are biosynthetic precursors of LAMs, are composed of a carbohydrate backbone comprising a core consisting of D-mannan and a mannosyl phosphatidylinositol (hereinafter referred to as PIM) anchor at the mannan reducing end of said core. LMs are devoid of a D-arabinan domain and the caps found in LAMs [12]. LMs are pro-inflammatory, but the inventors have recently described the fact that LMs of various bacterial origins, including *M. bovis* BCG, *M. tuberculosis*, *M. chelonae* and *M. kansasii*, also have considerable anti-inflammatory properties [13]. In particular, the triacylated and tetraacylated LMs of *Mycobacterium bovis* BCG induce macrophage stimulation and the expression of pro-inflammatory cytokines by means of TLR2, TLR4 and the MyD88 adapter protein [14], whereas the diacylated LMs and, to a certain extent, the triacylated LMs, inhibit the production of inflammatory cytokines by macrophages stimulated through the TLR4 pathway, independently of TLR2 [15]. Consequently, the degree of acylation influences the modulatory effect of the LMs of *M. bovis*. The authors have proposed that the differential acylation of the LMs of the mycobacterial wall may represent an additional means for regulating the inflammatory response of the host.

PIMs are low-molecular-weight (approximately 1000-2500) molecules comprising, in general, from 1 to 4 acylated chains, a phosphatidyl-myo-inositol residue and 1 to 6 mannose residues. Thus, natural PIMs may be in various forms with a varying number of mannose and acyl residues.

Among natural PIMs, phosphatidyl-myo-inositol dimannoside (hereinafter referred to as $PIM_2$) and phosphatidyl-myo-inositol hexamannoside (hereinafter referred to as $PIM_6$) are those most commonly found in *Mycobacterium bovis* BOG and *Mycobacterium tuberculosis* H37Rv. An example of $PIM_6$ structure in the natural state is represented in FIG. 1. It is noted that, in these natural structures, the mannosyl residues are borne by the D-myo-inositol in positions 2 and 6.

Several functions have recently been attributed to PIMs.

It has been demonstrated that PIMs are TLR2 agonists [3] and are recognized by human $CD4^-CD8^-$ α/β T cells in the context of antigen-presenting cells expressing CD1b [4]. The high-affinity interaction between CD1b proteins and the acylated side chains of $PIM_2$ has been established [5]. The phosphatidylinositol fraction appears to play a central role in the process of PIM binding to CD1b proteins. Moreover, it has been demonstrated that $PIM_2$ could increase the recruitment of NKT cells (Natural Killer T cells), which play an essential role in the granulomatous response [6], [7].

It has been found that the *Mycobacterium bovis* BCG, *Mycobacterium tuberculosis* H37Rv and *Mycobacterium smegmatis* 607 strains essentially contain two PIM families, dimannosylated PIMs ($PIM_2$) and hexamannosylated PIMs ($PIM_6$) [7]. $PIN_1$, $PIM_3$, $PIM_4$ and $PIM_5$ have been observed in small amounts, suggesting that they are biosynthetic intermediates. PIMs are synthesized from phosphatidylinositol by sequential addition of mannose residues at specific positions.

The three genes encoding the mannosyl transferases involved in the addition of the first three units of α-Manp are now known. The initiation step, catalyzed by the pimA enzyme [16], consists in transferring an α-Manp residue to the myo-inositol of the phosphatidylinositol so as to form $PIM_1$. The addition of a second α-Manp residue to the myo-inositol of the phosphatidylinositol so as to generate $PIM_2$ is catalyzed by the pimB enzyme [17]. The elongation occurs by means of pimC [18] so as to create $PIM_3$ through the addition of a third α-Manp residue.

Various acylated forms of PIMs, in particular $PIM_2$ and $PIM_6$, have been purified and characterized [7]. Four major acylated (monoacylated or tetraacylated) forms have been described for $PIM_2$ and $PIM_6$ ($Ac_1$- to $Ac_4$-$PIM_2$ and -$PIM_6$; see table 1). Their biological activity consisting in stimulating macrophages to produce cytokines has also been demonstrated.

TABLE 1

The major acylated forms of $PIM_6$ demonstrated in *M. bovis* BCG

| | Acyl | Gro | | Manp | Myo-Ins | |
|---|---|---|---|---|---|---|
| m/z | fragment | 1 | 2 | 6 | 3 | % |
| $Ac_1PIM_6$ 1543.6 | $C_{16}$ | $C_{16}$ | | | | |
| 1585.7 | $C_{19}$ | $C_{19}$ | | | | |
| $Ac_2PIM_6$ 1781.8 | $C_{16}, C_{16}$ | $C_{16}$ | $C_{16}$ | | | 35 |
| 1823.9 | $C_{16}, C_{19}$ | $C_{16}$ | $C_{19}$ | | | 65 |
| $Ac_3PIM_6$ 2062.1 | $2C_{16}, C_{19}$ | $C_{16}$ | $C_{19}$ | $C_{16}$ | | 100 |
| $Ac_4PIM_6$ 2300.3 | $3C_{16}, C_{19}$ | $C_{16}$ | $C_{19}$ | $C_{16}$ | $C_{16}$ | 56 |
| 2342.4 | $2C_{16}, 2C_{19}$ | $C_{16}$ | $C_{19}$ | $C_{16}$ | $C_{19}$ | 44 |

The relative abundance of the various species for each acylated form has been determined on the basis of the integration of the corresponding monoisotopic signals [19].

The inventors have previously shown that $PIM_2$ and $PIM_6$ induce a weak activation of macrophages so as to secrete TNF, via TLR2 and the adapter MyD88, irrespective of their acylated structure [7], [19].

However, since PIMs are precursors of LMs, and in view of the recent demonstration by the inventors that diacylated LM and triacylated LM have a strong anti-inflammatory effect, they have determined that certain natural PIMs, including diacylated $PIM_6$ and triacylated $PIM_6$, are inhibitors of pro-inflammatory cytokine release by macrophages. This work is the subject of French patent application No. 06/10136 of Nov. 20, 2006, published under number FR 2908658.

The complete syntheses of $PIM_2$ and of $PIM_6$ have been described [20]. The inventors have already carried out the synthesis of diacylated $PIM_1$ and have shown the inhibition of pro-inflammatory cytokine release.

As indicated above, there is a real medical need to find new inhibitors of pro-inflammatory cytokines such as TNF and IL-12 which overcome the faults, drawbacks and obstacles of the prior art inhibitors such as steroids or monoclonal antibodies.

The synthetic derivatives of PIMs may constitute an advantageous alternative for meeting this need.

Thus, there is a real need for novel synthetic derivatives of PIMs which are at the same time simple to synthesize, easy to use and inexpensive, and which have inhibitory properties on the expression of pro-inflammatory cytokines which are even greater than the prior art inhibitors.

DESCRIPTION OF THE INVENTION

The objective of the present invention is in fact to meet this need by providing novel compounds of general formula (I):

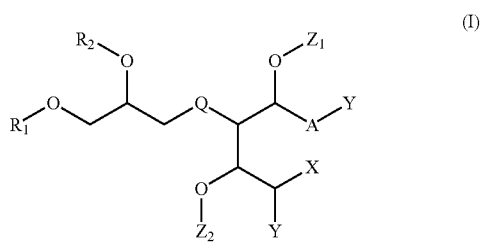

in which:

$R_1$ and $R_2$ represent, independently of one another, a hydrogen atom, a $C_1$-$C_{20}$ alkyl radical or a $C_1$-$C_{20}$ acyl radical, it being understood that, when one of the substituents $R_1$ or $R_2$ is a hydrogen atom, the other substituent is other than hydrogen;

$Z_1$ and $Z_2$ represent, independently of one another, a hydrogen atom, or at least one sugar chosen from the group comprising mannose, glucose and galactose, it being understood that, when one of the substituents $Z_1$ or $Z_2$ is a hydrogen atom, the other substituent is other than hydrogen;

Q represents —$OP(O)_2O$—, —$OCO_2$—, —$NHCO_2$— or —NHCONH—;

Y represents a hydrogen atom, a hydroxyl radical, a $C_1$-$C_6$ alkoxy radical, or —$(CH_2)_n$—OH, with n being an integer equal to 1, 2 or 3, it being understood that, when Y is a hydroxyl radical, $Z_1$ and $Z_2$ do not both represent a hydrogen atom;

A represents —$CH_2$—;

X represents a hydrogen atom;

or A and X together form a bond so as to result in a 6-membered ring in which:

A represents a —CH—,

X represents a —$CH_2$—, —CH(OH)—, an oxygen atom, an —$NR_3$— in which $R_3$ is a hydrogen atom, a $C_1$-$C_6$ alkyl radical or a $C_1$-$C_{20}$ acyl radical, it being understood that, when A and X form a bond so as to result in a 6-membered ring,

X=—CH(OH)—,

Y=—OH, and $Z_1$ and $Z_2$ represent, independently of one another, at least one sugar chosen from the group comprising mannose, glucose and galactose, the 6-membered ring is in the myo-inositol configuration with $Z_1$ or $Z_2$ in position 1 and representing at least one sugar;

or a pharmaceutically acceptable salt thereof.

In the context of the invention, the term "myo-inositol" is intended to mean the following structure with the numbering indicated according to the recommendations of the *International Union of Biochemistry* (1988).

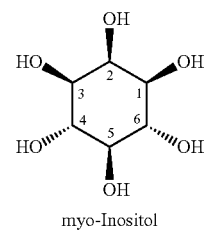 [SMILES: O[C@H]1[C@H](O)[C@@H](O)[C@H](O)[C@@H](O)[C@H]1O]

myo-Inositol

According to one embodiment of the invention, the compounds of the invention in which A and X together form a bond so as to result in a 6-membered ring may be of formula (Ia)

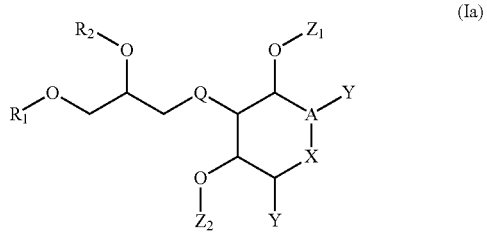

(Ia)

in which:
$R_1$ and $R_2$, $Z_1$ and $Z_2$, Q and Y are as defined above;
A represents a —CH—;
X represents a —CH$_2$—, —CH(OH)—, an oxygen atom, an —NR$_3$— in which $R_3$ is a hydrogen atom, a $C_1$-$C_6$ alkyl radical or a $C_1$-$C_{20}$ acyl radical, it being understood that, when
X=—CH(OH)—,
Y=—OH, and
$Z_1$ and $Z_2$ represent, independently of one another, at least one sugar chosen from the group comprising mannose, glucose and glactose,
the 6-membered ring is in the myo-inositol configuration with $Z_1$ or $Z_2$ in position 1 and representing at least one sugar;
or a pharmaceutically acceptable salt thereof.

An example of this embodiment can be a compound in which A and X together form a bond so as to result in a 6-membered ring, it being possible for said compound to then be a compound in which:
$R_1$ and $R_2$ represent, independently of one another, a $C_1$-$C_{20}$ acyl radical;
$Z_1$ represents a hydrogen atom;
$Z_2$ represents mannose;
Q represents —OP(O)$_2$O—;
A represents a —CH—;
X represents a —CH(OH)—;
Y represents a hydroxyl radical;
the 6-membered ring is in the myo-inositol configuration with $Z_1$ in position 1;
or a pharmaceutically acceptable salt thereof.

Another example of this embodiment can be a compound in which A and X together form a bond so as to result in a 6-membered ring, it being possible for said compound to then be a compound in which:
$R_1$ and $R_2$ represent, independently of one another, a $C_1$-$C_{20}$ acyl radical;
$Z_1$ represents mannose;
$Z_2$ represents a hydrogen atom;
Q represents —OP(O)$_2$O—;
A represents a —CH—;
X represents a —CH(OH)—;
Y represents a hydroxyl radical;
the 6-membered ring is in the myo-inositol configuration with $Z_1$ in position 1;
or a pharmaceutically acceptable salt thereof.

When A and X together form a bond so as to result in a 6-membered ring, the compounds of the invention can also be, for example, compounds in which:

$R_1$ and $R_2$ are as defined above;
Q represents —OP(O)$_2$O—;
A represents a —CH—;
X represents —CH(OH)—;
Y represents a hydroxyl radical;
$Z_1$ and $Z_2$ represent, independently of one another, at least one sugar chosen from the group comprising mannose, glucose and galactose, the 6-membered ring is in the myo-inositol configuration with $Z_1$ or $Z_2$ in position 1 and representing at least one sugar;
or a pharmaceutically acceptable salt thereof.

Still in the case where A and X together form a bond so as to result in a 6-membered ring, the compounds of the invention may further be, for example, compounds in which:
$R_1$ and $R_2$, $Z_1$ and $Z_2$ and Y are as defined above;
Q represents —OP(O)$_2$O—;
A represents a —CH—;
X represents an —NR$_3$— in which $R_3$ is a hydrogen atom, a $C_1$-$C_6$ alkyl radical or a $C_1$-$C_{20}$ acyl radical;
or a pharmaceutically acceptable salt thereof.

According to another embodiment of the invention, the compounds of the invention may be of formula (Ib)

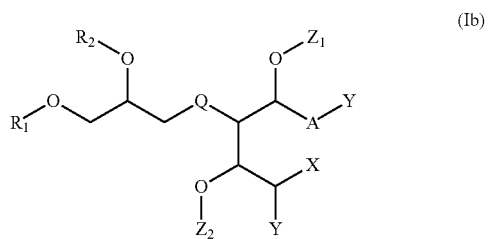

(Ib)

in which:
$R_1$ and $R_2$, $Z_1$ and $Z_2$, Q and Y are as defined above;
A represents —CH$_2$—;
X represents a hydrogen atom;
or a pharmaceutically acceptable salt thereof.

Entirely unexpectedly, it has been observed that the synthetic derivatives of PIMs in accordance with the invention make it possible to separate the property of these derivatives of acting as an agonist of TLR receptors involved in the immune response, and thus to separate the pro- and anti-inflammatory activity of these novel PIMs.

Moreover, the PIM derivatives according to the invention have low molecular weights (approximately 1000). They are well defined from a molecular point of view and they are easier to synthesize than natural PIMs. In addition, they are noncytotoxic.

Furthermore, these derivatives have an immunomodulatory activity which is at least comparable to, and preferably greater than, that of natural PIMs.

For the purpose of the present invention, the term "alkyl" is intended to mean a linear, branched or cyclic, saturated or unsaturated, optionally substituted, carbon radical containing 1 to 20 carbon atoms, for example 1 to 15 carbon atoms, for example 1 to 6 carbon atoms. By way of illustration, mention may be made of methyl, ethyl, propyl, butyl, isobutyl, pentyl, hexyl, octyl, nonyl, decyl, undecyl, dodecanyl, tridecanyl, tetradecanyl, pentadecanyl, hexadecanyl, heptadecanyl, octadecanyl, nonadecanyl and eicosanoyl radicals, and branched isomers thereof.

For the purpose of the present invention, the term "acyl" is intended to mean a —COR' radical in which R' is an alkyl radical as defined above. The acyl group can also signify the tuberculostearyl group.

For the purpose of the present invention, the term "alkoxy" is intended to mean an —OR' radical in which R' is an alkyl radical as defined above.

In the context of the present invention, the term "pharmaceutically acceptable salts" comprises the salts prepared with nontoxic acids or bases depending on the substituents present on the compounds. When the compounds of the invention comprise acid functions, the corresponding salts can be obtained by addition of an organic or inorganic base to the compound in neutralized form, optionally in the presence of a solvent, preferably an inert solvent. Examples of salts of addition of a base may be the sodium, potassium, calcium, ammonium, amino (organic) or magnesium salts. When the compounds of the invention comprise basic functions, the corresponding salts can be obtained by addition of an organic or inorganic acid, optionally in a solvent, preferably an inert solvent. Examples of inorganic acid addition salts can be the salts of hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid or hydriodic acid. Examples or organic acid addition salts can be the salts of acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid or methanesulfonic acid. Also covered by this invention are salts of amino acids such as arginate, and salts of organic acids such as glucuronic acid or galacturonic acid.

The compounds of general formulae (I), (Ia) and (Ib) may be in racemic form or in a form enriched in an enantiomer or enriched in a stereoisomer.

One of the preferred compounds of the invention is the compound of formula (Ia) having the following structure (isoPIM$_1$-C16C18):

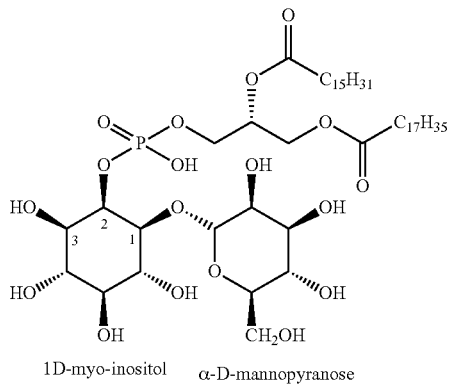

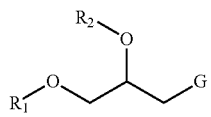

The invention also relates to the method for preparing compounds according to the invention as defined above, in which:
a) a di-O-acylated or di-O-alkylated derivative of glycerol of formula (III)

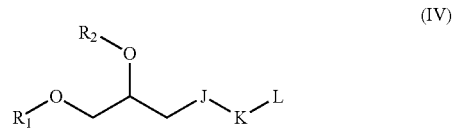

in which:
G=OH or NH$_2$,
R$_1$ and R$_2$ have the same definitions as above,
is condensed with a phosphitylating, phosphorylating or carbonylating agent so as to give an intermediate of formula (IV)

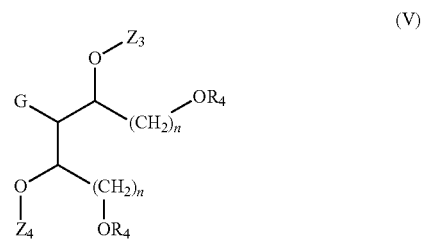

in which:
J=O or NH,
K=P—OBn, P(O)—OBn or C=O,
L=leaving group,
R$_1$ and R$_2$ have the same definitions as above;
b) the intermediate (IV) is condensed with a derivative of a polyol or aminopolyol of general formula (V)

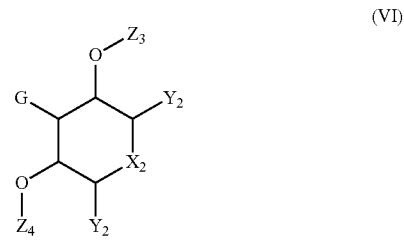

in which:
G=OH or NH$_2$,
Z$_3$ and Z$_4$ represent, independently of one another, a hexopyranose of manno, gluco or galacto configuration and bearing acetyl or methoxyacetyl protective groups, or a benzyl group, it being understood that at least one of the Z$_3$ and Z$_4$ groups represents a protected sugar,
R$_4$ represents a protective group chosen from the group comprising a benzyl group or a C$_1$-C$_6$ alkoxyacetyl radical,
or the intermediate (IV) is condensed with a cyclic compound of general formula (VI)

in which:
G=OH or NH$_2$,
Z$_3$ and Z$_4$ have the same definitions as above,
Y$_2$=H or an —OR$_4$ group or a —(CH$_2$)$_n$OR$_4$ group in which R$_4$ has the same definition as above,
X$_2$=—CH$_2$, —CHOR$_4$, —NR$_3$ or O in which R$_3$ is a hydrogen atom, a C$_1$-C$_6$ alkyl radical or a C$_1$-C$_{20}$ acyl radical and R$_4$ represents a protective group, such as a benzyl group, or a C$_1$-C$_6$ alkoxyacetyl radical, optionally in the presence of a coupling agent;

c) the compound obtained in step b) is optionally subjected to an oxidation reaction, so as to give a compound of general formula (VII)

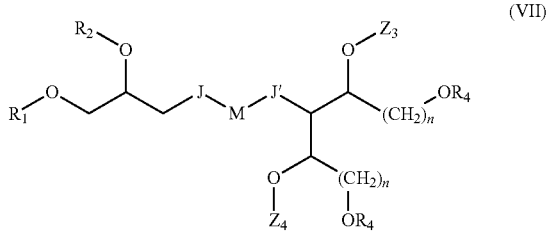

(VII)

in which:

J and J'=O or NH,

M=P(O)OBn or C=O, $Z_3$, $Z_4$, $R_1$, $R_2$ and $R_4$ have the same definitions as above, or a compound of general formula (VIII)

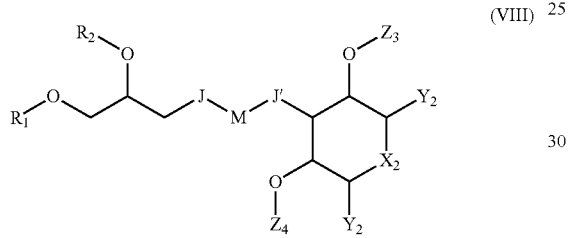

(VIII)

in which:

J and J'=O or NH,

M=P(O)OBn or C=O, $X_2$, $Y_2$, $Z_3$, $Z_4$, $R_1$, $R_2$ and $R_4$ have the same definitions as above;

d) the product of general formula (VII) or of general formula (VIII) is subjected to a two-stage deprotection which consists in first treating with an alkylamine chosen from the group comprising t-butylamine, so as to selectively cleave the acetyl or methoxyacetyl groups, and then in subjecting the deacylated products to catalytic hydrogenation in order to eliminate the benzyl groups.

As examples of phosphitylating agents, mention may be made of chlorobis(diisopropylamino)phosphine, benzyloxydichlorophosphine, bis(benzyloxy)-N,N-diethylaminophosphine and related compounds.

As examples of phosphorylating agents, mention may be made of diphenyl chlorophosphate, dibenzyl phosphorochloridate, xylene chlorophosphate and related compounds.

As examples of carbonylating agents, mention may be made of carbonyldiimidazole, triphosgene and related compounds.

The term "protective group" is intended to mean a group which allows the conversion of a functional group into a group which will be inert under the chosen reaction conditions in order to prevent side reactions occurring in the rest of the synthesis. In this respect, mention may be made, for example, of the benzyl group, the t-butyldimethylsilyl group, the acetyl group or the methoxyacetyl group.

The term "leaving or departing group" is intended to mean a group which can be substituted with a nucleophilic reactant, for instance halides or tosylates.

In the context of the present invention, the term "coupling agent" or "bonding agent" is intended to mean an agent which allows the condensation of a derivative of phosphoric acid or of a carboxylic acid with an alcohol or an amine so as to form the corresponding ester or amide bonds. In this respect, mention may be made, for example, of dicyclohexylcarbodiimide (DCC) or N-ethyl-N-dimethylaminopropylcarbodiimide (EDCI).

In one embodiment of the invention, the compounds of formula (I) in which Q represents —OP(O)$_2$O— can also be prepared according to a method in which:

a) a di-O-acylated or di-O-alkylated derivative of glycerol of formula (IX)

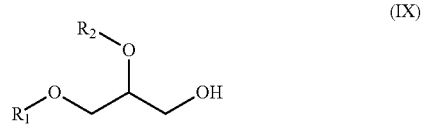

(IX)

in which $R_1$ and $R_2$ have the same definitions as above, is condensed with a phophitylating agent, so as to give an intermediate of formula (X)

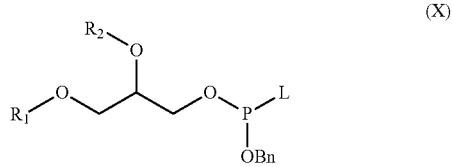

(X)

in which L=leaving group;

b) the intermediate (X) is then condensed with a derivative of a polyol of general formula (XI)

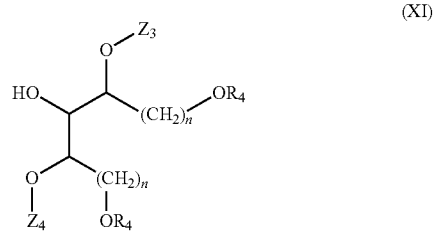

(XI)

in which:

$Z_3$ and $Z_4$ represent, independently of one another, a hexopyranose of manno, gluco or galacto configuration and bearing acetyl or methoxyacetyl protective groups, or a benzyl group, with the proviso that at least one of the $Z_3$ and $Z_4$ groups represents a protected sugar, $R_4$ represents a protective group, such as a benzyl group, or a $C_1$-$C_6$ alkoxyacetyl radical, or with a cyclic compound of general formula (XII)

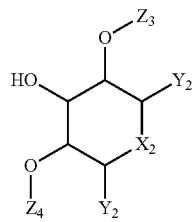

(XII)

in which:
Z$_3$ and Z$_4$ have the same definitions as above,
Y$_2$=H or an —OR$_4$ group or a —(CH$_2$)$_n$OR$_4$ group in which R$_4$ has the same definition as above and n can take values of 1 to 3,
X$_2$=—CH$_2$, —CHOR$_4$, —NR$_3$ or O in which R$_3$ and R$_4$ have the same definition as above,
in the presence of a coupling agent chosen from the group comprising 1H-tetrazole;
c) the intermediate phosphite is then subjected to an oxidation reaction, so as to give a compound of general formula (XIII)

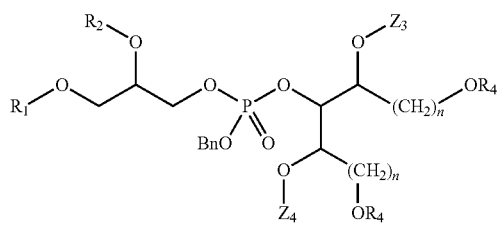

(XIII)

in which Z$_3$, Z$_4$, R$_1$, R$_2$ and R$_4$ have the same definitions as above,
or a compound of general formula (XIV)

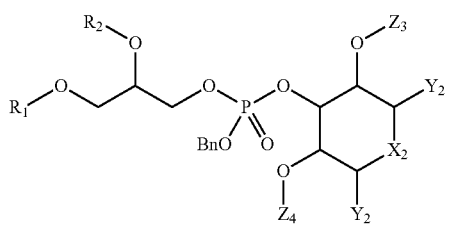

(XIV)

in Which X$_2$, Y$_2$, Z$_3$, Z$_4$, R$_1$ and R$_2$ have the same definitions as above;
d) the compounds (XIII) and (XIV) obtained in step c) are then subjected to a two-stage deprotection which consists in first treating them with an alkylamine such as t-butylamine, so as to selectively cleave the acetyl or methoxyacetyl groups, and then in subjecting the deacylated products to catalytic hydrogenation in order to eliminate the benzyl groups.

Another subject of the present invention is a pharmaceutical composition comprising at least one compound according to the invention as defined above and any pharmaceutically acceptable excipient.

The composition according to the invention may also comprise components well known to those skilled in the art in the pharmaceutical field, such as stabilizers, emulsifiers, tonicity agents, preservatives, dyes, excipients, binders or lubricants, in particular.

The pharmaceutical composition according to the invention can be used for preventing or treating inflammatory or autoimmune disorders or diseases.

Another subject of the invention consists of the use of a composition as described above, for the production of a medicament intended for the prevention or treatment of a disease associated with the overexpression of cytokines or of chemokines, in particular of TNF and/or of IL-12, in an individual.

The term "individual" is intended to mean a mammal, preferably a human.

The disease associated with the overexpression of cytokines or of chemokines, in particular of TNF and/or of IL-12, comprises:
A) immune or autoimmune diseases chosen from the group comprising rheumatoid arthritis, sugar diabetes, systemic lupus erythematosus or Basedow's disease;
B) transplant rejection;
C) viral and/or parasitic infections;
D) shocks resulting from a chronic or acute infection of bacterial, viral and/or parasitic origin;
E) inflammatory diseases chosen from the group comprising chronic inflammatory diseases (sarcoidosis, inflammatory bowel disease, rheumatoid arthritis, ulcerative colitis, Crohn's disease) and vascular inflammatory diseases (defibrination syndrome, artherosclerosis, Kawazaki disease);
F) neurodegenerative diseases chosen from the group comprising demyelinating diseases (multiple sclerosis and acute transverse myelitis), extrapyramidal and cerebellar diseases (lesions of the corticospinal system or disorders of the basal ganglia);
G) malignant pathological conditions involving TNF-secreting tumors or involving TNF, chosen from the group comprising leukemia (acute, chronic myelodisplastic, lymphocytic or myelocytic), lymphoma (Hodgkin's or malignant (Burkitt's)); and
H) alcohol-induced hepatitis.

The invention also relates to the use of a compound as defined above, for the production of a medicament intended for the prevention or treatment of a disease associated with the overexpression of cytokines or of chemokines, in particular of TNF and/or of IL-12, said disease comprising:
A) immune or autoimmune diseases chosen from the group comprising rheumatoid arthritis, diabetes mellitus, systemic lupus erythematosus or Basedow's disease;
B) transplant rejection;
C) viral and/or parasitic infections;
D) shocks resulting from a chronic or acute infection of bacterial, virual and/or parasitic origin;
E) inflammatory diseases chosen from the group comprising chronic inflammatory diseases and vascular inflammatory diseases;
F) neurodegenerative diseases chosen from the group comprising demyelinating diseases, and extrapyramidal and cerebellar diseases;
G) malignant pathological conditions involving TNF-secreting tumors or involving TNF, chosen from the group comprising leukemia and lymphoma; and
H) alcohol-induced hepatitis.

Preferably, said medicament is intended for the prevention or treatment of an inflammatory disease in an individual.

Said medicament can be administered by injection (intravenous, intramuscular, subcutaneous, intracutaneous, etc.), nasal, oral or percutaneous administration or by inhalation.

Depending on the mode of administration, said medicament can be prepared in the form of solutions, emulsions, tablets, powders, ointments, lotions, gels, suppositories or sprays.

In said medicament, the concentration of compound of formula (I) or of pharmaceutically acceptable salt thereof is not limited and is preferably between 0.1% and 100% (w/w), and particularly preferably between 0.5% and 20%.

Other advantages may further appear to those skilled in the art on reading the examples below, illustrated by the appended figures, given by way of illustration.

BRIEF DESCRIPTION OF THE FIGURES

FIG. 2a), for the compound of example 2 $isoPIM_1-C_{16}C_{18}$ (SFPIM219; FIG. 2b) and for the compounds of examples 3 and 4 $PIM-2-mimNCOCF_3$ $_{(SFPIM}324-t4)$ and PIM-2-mimNH(SFPIM324-t8) (FIG. 2c).

EXAMPLES

Solvents and Reactants

The dichloromethane ($CH_2Cl_2$) and the toluene are distilled, under an argon atmosphere, over $CaH_2$, and the tetrahydrofuran (THF) is distilled, under an argon atmosphere, over sodium and benzophenone. The diethyl ether is distilled, under an argon atmosphere, over $CaH_2$ and stored at 0-4° C. under an argon atmosphere on 4 Å molecular sieve. The other solvents used come from the supplier Carlo-Erba.

Nuclear Magnetic Resonance (NMR)

The $^1H$ and $^{13}C$ spectra are performed on a Bruker DPX250 instrument on a Bruker AV400 instrument. The chemical shifts (δ) of the $^1H$ NMR spectra are calibrated according to the tetramethylsilane (TMS) control having the δ value of 0.00 ppm. The δ of the $^{13}C$ NMR spectra are calibrated on the reference value of the solvent as described in the article Gottlieb et al., J. Org. Chem., 1997, 62, 7512. The $^{31}P$ NMR spectra are formed on a Bruker AV400 instrument and are calibrated according to an external reference containing 80% of phosphoric acid ($H_3PO_4$) (δ=0.00 ppm). The $^{19}F$ spectra are recorded on a Bruker AV400 instrument equipped with an automatic multinuclear probe and are calibrated according to an external reference containing $BF_3$ etherate (δ=0.00 ppm). The measurements are carried out at 25° C. in tubes 5 mm in diameter.

The spectra are performed in deuterated solvents which come from the supplier Aldrich or SDS.

Chromatography

The thin layer chromatographies (TLC) are carried out on "TLC Silica gel $60F_{254}$" aluminum plates from Merck. The compounds are visualized under a UV lamp and/or are dipped in the developer comprising phosphomolybdic acid in sulfuric acid and ethanol, followed by heating with a heat stripper.

The chromatography columns are prepared with a silica gel (Silica gel 60 (40-63 µm)) from Merck.

Mass Spectrometry

ESI mass spectrometry: The samples are analyzed on a Perkin Elmer Sciex API 300 spectrometer in solvents of "analytical" quality.

High-resolution mass spectrometry: The samples are analyzed at the center for physical measurements of the Blaise Pascal university in Aubière.

Example 1

1) Synthesis of isoPIM$_1$-2C$_{16}$ (SFPIM91)

Figure 1:
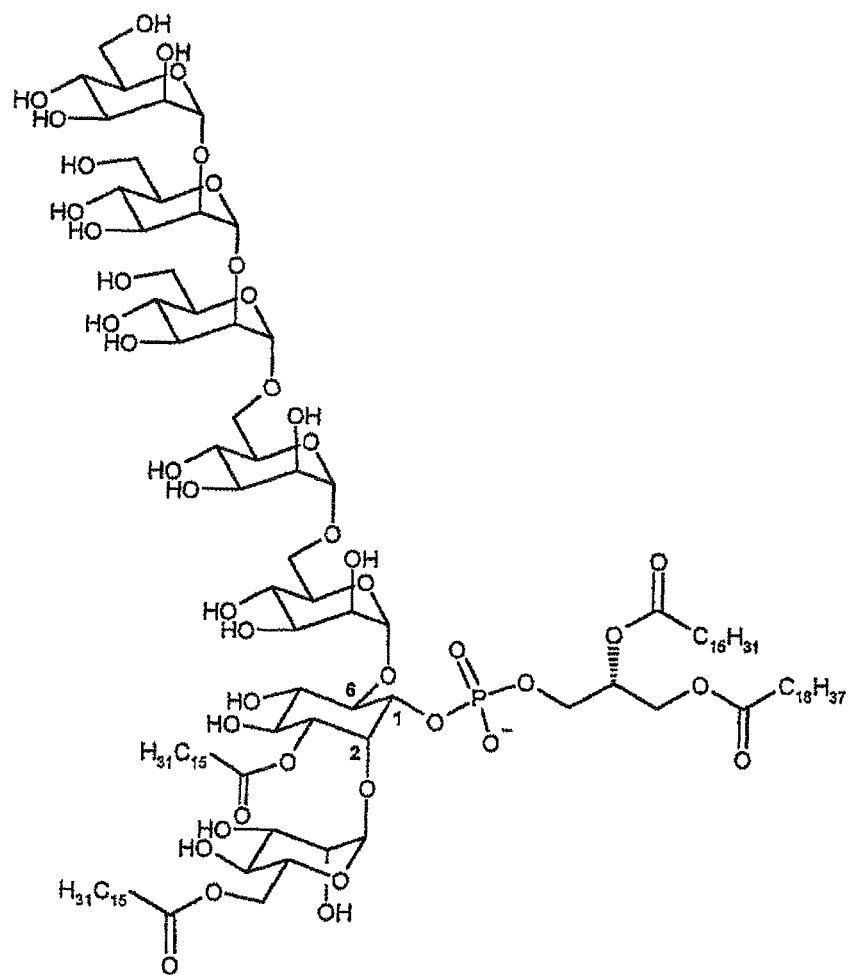
FIG. 1 represents a structure of natural $PIM_6$ comprising three acyl groups of which the alkyl chain is linear and $C_{16}$, and one acyl group of which the alkyl chain is branched and $C_{19}$.
Figure 2A:
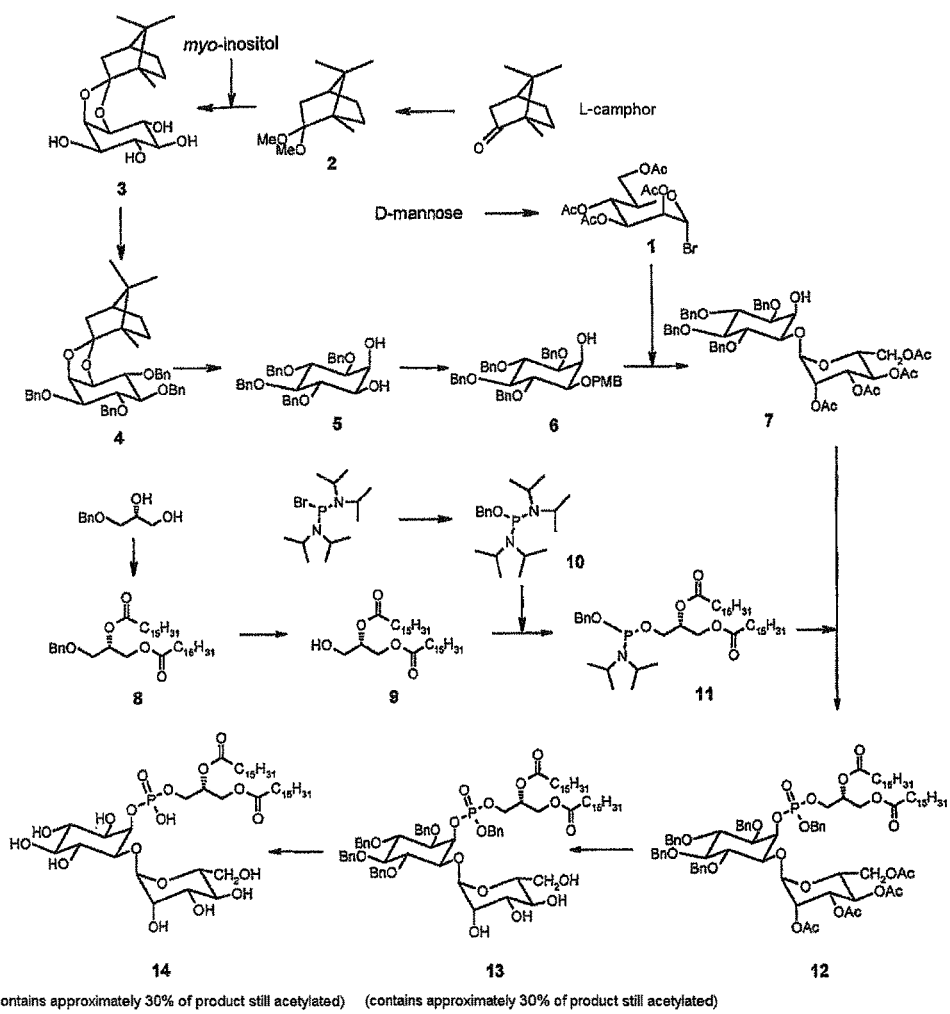
FIGS. 2a, 2b and 2c represent the synthesis scheme for the compound of example 1 $isoPIM_1PIM1-2C_{16}$ (SFPIM91.

L-camphor dimethyl acetal (Compound 2, FIG. 2a)

SFPIM-97

Preparation according to Lindberg et al. *Tetrahedron*, 2002, 58, 1387-1398 [24]. Sulfuric acid ($H_2SO_4$) (194 µl) is added to a solution of commercial L-camphor (>95%, Fluka) (20 g, 0.131 mol) in a mixture of trimethyl orthoformate (95 ml, 0.908 mol, 6.9 eq) and methanol (20 ml). After 48 h of stirring, the mixture is neutralized by adding sodium methoxide (NaOMe) (400 mg) and the solvents are evaporated off. The residue is collected by distillation under vacuum (25 mbar) at 125° C., so as to give the compound 2 (21 g, 81%) in the form of a colorless liquid. $^1$H-NMR spectrum conforms.

1,2-O-(L-1,7,7-trimethylbicyclo[2,2,1]hept-6-ylidene)-D-myo-inositol (Compound 3, FIG. 2a)

SFPIM-10

Preparation according to Lindberg et al. Tetrahedron, 2002, 58, 1387-1398 [24]. Sulfuric acid $H_2SO_4$ (173 µl) is added to a solution of compound 2 (8.06 g, 0.041 mol, 2.4 eq) and commercial myo-inositol>99% (Aldrich) (3.1 g, 0.017 mol) in dimethyl sulfoxide (DMSO) (34 ml). The resulting mixture is stirred for 3 h at 75° C., and then neutralized by adding $Et_3N$ (1 ml), and concentrated under vacuum at 80° C. DMSO (3 ml), chloroform ($CHCl_3$) (52 ml), methanol (MeOH) (3.2 ml), water ($H_2O$) (1 ml) and p-toluenesulfonic acid (PTSA) (11.6 mg) are added to the residue. The reaction mixture is stirred for 18 h and then neutralized by adding $Et_3N$ (0.4 ml). The precipitate thus formed is filtered off through sintered glass and washed with $CHCl_3$ (2×40 ml). The crude product is recrystallized from methanol (MeOH) (containing 0.1% $Et_3N$), to give the compound 3 (1.738 g, 32%) in the form of a white solid. $^1$H-NMR spectrum conforms.

3,4,5,6-tetra-O-benzyl-1,2-O-(L-1,7,7-tetramethyl-bicyclo[2,2,1]hept-6-ylidene)-D-myo-inositol (Compound 4, FIG. 2a)

SFPIM-72

Sodium hydride (NaH) (1.16 g, 0.048 mol, 12 eq, 60% as a dispersion in mineral oil) is added, under an argon atmosphere, to a solution, cooled beforehand to 0° C., of compound 3 (1.266 g, 4.02 mmol) in anhydrous DMF (30 ml). After 15 m of stirring at 0° C., benzyl bromide (2.9 ml, 0.024 mmol, 6 eq) is added dropwise, and then the reaction mixture is stirred for 24 h at ambient temperature (approximately 20° C.). It is then cooled to 0° C., and then excess NaH is destroyed by adding MeOH (3 ml) and the medium is diluted with toluene (250 ml). The organic phase is washed with water (100 ml), then with a saturated solution of NaCl (3×100 ml), and then dried over $MgSO_4$. The solvents are evaporated off and purification by silica gel column chromatography (8/1 hexane/diethyl ether) results in the compound 4 (2.15 g, 80%) in the form of a colorless syrup.

$C_{44}H_{50}O_6$ (M=674.89 g/mol).

$^1$H NMR (400 MHz, $CDCl_3$) δ 0.86 (s, 3H, $CH_3$), 0.87 (s, 3H, $CH_3$), 1.09 (s, 3H, $CH_3$), 1.22-1.33 (m, 3H), 1.34-1.45 (b, 1H), 1.47 (s, 0.5H), 1.50 (s, 0.5H), 1.68-1.76 (m, 2H), 1.9-2.02 (m, 2H), 3.44 (dd, 1H, H5, $J_{5-6}$=8.2 Hz, $J_{4-5}$=9.6 Hz), 3.74 (dd, 1H, H4, $J_{4-3}$=7.2 Hz), 3.77 (t, 1H, H1, $J_{1-2}$=4.2 Hz), 3.84 (dd, 1H, H6, $J_{1-6}$=8.4 Hz), 3.96 (dd, 1H, H3, $J_{2-3}$=6.2 Hz), 3.44 (dd, 1H, H5, $J_{5-6}$=8.2 Hz, $J_{4-5}$=9.6 Hz), 4.30 (dd, 1H, H2), 7.20-7.45 (m, 20H, 4Ph).

$^{13}$C NMR (100 MHz, $CDCl_3$) δ 10.27 ($CH_3$), 20.52 ($CH_3$), 20.75 ($CH_3$), 27.76 ($CH_2$), 29.89 ($CH_2$), 45.08 ($CH_2$), 45.31 (CH), 48.08 (Cq), 51.67 (Cq), 72.55 ($CH_2$, $CH_2Ph$), 73.19 (CH, C2), 74.00 ($CH_2$, $CH_2Ph$), 75.08 ($CH_2$, $CH_2Ph$), 75.25 ($CH_2$, $CH_2Ph$), 76.32 (CH, C3), 77.50 (CH, C1), 80.86 (CH, C6), 82.22 (CH, C5), 83.31 (CH, C4), 117.77 (Cq), 127.55-128.44 (CH, Ph), 138.55-138.89 (Cq, Ph, 4 lines).

SI-MS: M calculated 674.36. found: 675.5 $[M+H]^+$, 692.5 $[M+NH_4]^+$, 697.5 $[M+Na]^+$, 713.5 $[M+K]^+$.

3,4,5,6-Tetra-O-benzyl-D-myo-inositol (Compound 5, FIG. 2a)

SFPIM-17

The compound 4 (1.53 g, 2.26 mmol) is suspended in an aqueous 80% acetic acid solution (75 ml) and the medium is stirred at 100° C. for 4 h. The solvents are evaporated off under vacuum and then coevaporated with toluene. The residue is purified by silica gel column chromatography (toluene/acetone 35/1 with a gradient up to 10/1), so as to result in the compound 5 (1.029 g, 84%) in the form of a white solid.

$C_{34}H_{36}O_6$ (M=540.66 g/mol).

$^1$H NMR (400 MHz, $CDCl_3$) δ 2.53 (d, 1H, OH-1, $J_{1-OH}$=4.8 Hz), 2.64 (s, 1H, OH-2), 3.42-3.51 (m, 3H, H3, H1, H5), 3.83 (dd, 1H, H6, $J_{6-5}$=9.6 Hz, $J_{1-6}$=9.6 Hz), 3.97 (dd, 1H, H4, $J_{3-4}$=9.6 Hz, $J_{4-5}$=9.6 Hz), 4.17 (dd, 1H, H2, $J_{2-3}$=2.8 Hz, $J_{2-1}$=2.8 Hz), 4.65-4.96 (m, 8H, 4 $CH_2Ph$), 7.25-7.4 (m, 20H, 4×5 $CH_{Ar}$).

$^{13}$C NMR (100 MHz, $CDCl_3$) δ 69.33 (CH, C2), 71.87 (CH, C1), 72.84 ($CH_2$, $CH_2Ph$), 75.71 ($CH_2$, $CH_2Ph$), 75.82 ($CH_2$, $CH_2Ph$), 76.07 ($CH_2$, $CH_2Ph$), 80.11 (CH, C3), 81.45 (CH, C6), 81.74 (CH, C4), 83.33 (CH, C5), 127.73-128.67 (CH, Ph, 9 lines), 137.89 (Cq, Ph), 138.62 (2Cq, Ph), 138.73 (Cq, Ph).

SI-MS: M calculated 540.25. found: 541.5 $[M+H]^+$, 558.5 $[M+NH_4]^+$, 563.5 $[M+Na]^+$, 579.5 $[M+K]^+$.

3,4,5,6-Tetra-O-benzyl-1-O-p-methoxybenzyl-D-myo-inositol (Compound 6, FIG. 2a)

SFPIM104

A suspension of compound 5 (301 mg, 0.557 mmol) and dibutyltin oxide (139 mg, 0.557 mmol, 1 eq) in toluene (5 ml) is heated for 18 h at 140° C. under argon using a Dean-Stark trap in order to capture the water formed. The medium is concentrated under vacuum and the residue is dissolved in anhydrous DMF containing cesium fluoride (CsF) (172 mg, 1.11 mmol) and 4-methoxybenzyl chloride (76 µl, 0.557 mmol, 1 eq). The reaction is stirred for 7 h30 and the solvents are then evaporated to dryness so as to leave a solid white residue which is partially dissolved in ethyl acetate (20 ml). The residual solid is removed by filtration through sintered glass and the filtrate is evaporated to dryness. The residue is purified by silica gel column chromatography (7/3 petroleum ether/ethyl acetate) so as to result in the compound 6 (262 mg, 71%) in the form of a white solid.

$C_{42}H_{44}O_7$ (M=660.81 g/mol).

$^1$H NMR (400 MHz, CDCl$_3$) δ 2.43 (s, 1H, OH), 3.27 and 3.28 (2 dd, 2H, H1 and H3, $J_{1-6}=J_{3-4}$=9.6 Hz, $J_{1-2}=J_{2-3}$=2.8 Hz), 3.36 (dd, 1H, H5, $J_{5-6}=J_{5-4}$=9.2 Hz), 3.69 (s, 3H, CH$_3$), 3.89 and 3.91 (2 dd, 2H, H4 and H6), 4.09 (dd, 1H, H2, $J_{2-3}=J_{2-1}$=2.8 Hz), 4.53 (s, 2H, CH$_2$Ph), 4.61 (s, 2H, CH$_2$Ph), 4.72-4.83 (m, 6H, 3×CH$_2$h), 6.74 and 6.76 (2s, 2H, CH$_{Ar}$ PMB), 7.1-7.3 (m, 23H, CH$_{Ar}$).

$^{13}$C NMR (100 MHz, CDCl$_3$) δ 55.33 (CH$_3$), 67.59 (CH, C2), 72.44 (CH$_2$), 72.76 (CH$_2$), 75.95 (CH$_2$), 75.98 (2×CH$_2$), 79.55 and 79.86 (2 CH, C1 and C3), 81.27 and 81.29 (2 CH, C4 and C6), 83.26 (CH, C5), 127.61-129.59 (CH$_{Ar}$, 8 lines), 130.10 (Cq), 138.05 (Cq), 138.77 (Cq), 138.83 (Cq), 138.88 (Cq), 159.42 (Cq).

3,4,5,6-Tetra-O-benzyl-1-O-(2,3,4,6-tetraacetyl-α-D-mannopyranosyl)-D-myo-inositol (Compound 7, FIG. 2a)

SFPIM63

A solution of the compound 6 (457 mg, 0.69 mmol, 1 eq) in CH$_2$Cl$_2$ (10 ml) is delivered via a cannula-like tube, under argon, into a solution of the compound 1 (845 mg, 2.08 mmol, 3 eq) in CH$_2$Cl$_2$ (10 ml). The reaction mixture is stirred in the presence of 4 Å molecular sieve for 20 min, and then is cooled to −20° C. Silver triflate is added (1.066 g, 4.15 mmol, 6 eq) and the reaction medium is stirred, while allowing the temperature to come back up to 20° C., for 1 h. The reaction is neutralized by adding triethylamine (1 ml), and then diluted with CH$_2$Cl$_2$. The organic phase is washed with a saturated solution of NaHCO$_3$ (30 ml) and then of NaCl (30 ml) and is dried over MgSO$_4$. The solvent is evaporated off under vacuum and the residue is purified by silica gel column chromatography (3/1 petroleum ether/ethyl acetate) so as to result in the compound 7 (309 mg, 21%).

$C_{48}H_{54}O_{15}$ (M=870.96 g/mol).

$^1$H NMR (400 MHz, CDCl$_3$) δ 7.38-7.20 (m, 20H, CH$_{Ar}$), 5.43 (dd, 1H, H3', $J_{3'-2'}$=2.6 Hz, $J_{3'-4'}$=10 Hz), 5.34 (dd, 1H, H2', $J_{2'-1'}$=1 Hz), 5.27 (dd, 1H, H4', $J_{4'-5'}$=10 Hz), 5.07 (d, 1H, H1', $J_{1-2'}$=1 Hz), 4.86 (s, 4H, 2 CH$_2$Ph), 4.85 (d, 1H, CH$_2$Ph, J=10.8 Hz), 4.80 (d, 1H, CH$_2$Ph, J=10.8 Hz), 4.75 (d, 1H, CH$_2$Ph, J=11.2 Hz), 4.68 (d, 1H, CH$_2$Ph, J=11.2 Hz), 4.29 (m, 3H, H2, H5', H6A'), 4.03 (m, 2H, H$_6$B', H4 or H6), 3.95 (dd, 1H, $J_{5-4}=J_{5-6}$=9.6 Hz), 3.54 (dd, 1H, H1 or H3, J=2.8 and 10 Hz), 3.45 (dd, 1H, H4 or H6), 3.43 (dd, 1H, H3 or H1), 2.08 (s, 3H, CH$_3$ Ac), 2.06 (s, 3H, CH$_3$ Ac), 2.03 (s, 3H, CH$_3$ Ac), 2.00 (s, 3H, CH$_3$ Ac).

$^{13}$C NMR (100 MHz, CDCl$_3$) δ 170.74, 169.94, 169.91, 169.72, 138.68, 138.64, 138.33, 137.87, 128.65-127.75, 99.85 (C1'), 83.12, 81.27, 81.07, 80.42, 80.13, 76.28, 76.07, 76.01, 73.15, 69.64 (C2'), 69.54 (C5'), 69.20 (C3'), 68.92 (C2), 66.65 (C4'), 63.16 (C6'), 20.86, 20.78.

SI-MS: M calculated 870.35. found: 888.5 [M+NH$_4$]$^+$, 893.5 [M+Na]$^+$, 909.0 [M+K]$^+$.

3-O-Benzyl-1,2-O-dipalmitoyl-sn-glycerol (Compound 8, FIG. 2a)

SFPIM77

[(Dimethylamino)propyl]carbodiimide (EDCI) hydrochloride (847 mg, 4.42 mmol, 3 eq) and DMAP (54 mg, 0.44 mmol, 0.3 eq) are added, under an argon atmosphere, to a solution of 3-O-benzyl-sn-glycerol (268 mg, 1.47 mmol, 1 eq) and palmitic acid (943 mg, 3.68 mmol, 2.5 eq) in anhydrous CH$_2$Cl$_2$ (20 ml). The reaction mixture is stirred for 18 h at ambient temperature (approximately 20° C.) and then diluted with CH$_2$Cl$_2$ (100 ml). The organic phase is washed with a 1N HCl solution (50 ml), water (50 ml), and then a saturated solution of NaCl (50 ml) and dried over MgSO$_4$. The solvent is evaporated off under vacuum and the residue is purified by silica gel column chromatography (6/1 petroleum ether/ethyl acetate) so as to result in the compound 8 (909 mg, 93%) in the form of a white solid.

$C_{42}H_{74}O_5$ (M=659.06 g/mol).

$^1$H NMR (400 MHz, CDCl$_3$) δ 0.88 (t, 3H, CH$_3$), 1.25 (b, 48H, 24 CH$_2$), 1.59 (b, 4H, 2×2H3"), 2.28 (t, 2H, J=7.5 Hz), 2.32 (t, 2H, J=7.5 Hz), 3.59 (d, 2H, 2H3a), 4.19 (dd, 1H, H1a$_A$, $J_{1aA-1aB}$=12 Hz, $J_{1A-2a}$=6.4 Hz), 4.35 (dd, 1H, H1a$_B$, $J_{1aB-2a}$=3.6 Hz), 4.53 (AB, 2H, CH$_2$Ph, J=12.2 Hz), 5.24 (m, 1H, H2a), 7.32 (m, 5H, CH$_{Ar}$)

SI-MS: M calculated 658.55. found: 660.0 [M+H]$^+$, 677.0 [M+NH$_4$]$^+$, 682.0 [M+Na]$^+$.

1,2-O-dipalmitoyl-sn-glycerol (Compound 9, FIG. 2a)

SFPIM82

The compound 8 (890 mg, 1.35 mmol) is dissolved in a CH$_2$Cl$_2$/EtOH mixture (1/1.5, 25 ml). A large excess of palladium-on-carbon (Pd/C 10%) is added and the reaction is stirred for 4 h at ambient temperature (approximately 20° C.) under atmospheric hydrogen pressure (balloon). The reaction mixture is heated to 40° C. for better dissolution of the expected product and then the catalyst is removed by filtration through a millipore membrane. The solid is rinsed three times with 20 ml of CH$_2$Cl$_2$/EtOH mixture (1/1) preheated to 40° C. The residual solvents are evaporated off under vacuum, so as to result in the expected compound 9 (757 mg, 99%) in the form of a white solid.

$C_{25}H_{68}O_5$ (M=568.93 g/mol).

$^1$H NMR (250 MHz, CDCl$_2$) δ 0.88 (t, 6H, 2 CH$_2$, J=6.8 Hz), 1.26 (m, 48H, 24 CH$_2$), 1.62 (m, 4H, 2H3"), 1.99 (t, 1H, OH, J=6.5 Hz), 2.32 (t, 2H, J=7.7 Hz), 2.35 (t, 2H, J=7.5 Hz), 3.73 (dd, 2H, 2H3a, J=5 and 6.2 Hz), 4.23 (dd, 1H, H1a$_A$, $J_{1aA-1aB}$=12 Hz, $J_{1A-2a}$=5.5 Hz), 4.35 (dd, 1H, H1a$_B$, $J_{1aB-2a}$=4.5 Hz), 5.08 (m, 1H, H2a).

SI-MS: M calculated 568.51. found: 570.0 [M+H]$^+$, 587.0 [M+NH$_4$]$^+$, 592.0 [M+Na]$^+$.

(S)-2,3-Dipalmitoyloxypropyl benzyl (N,N-diisopropyl-amino)phosphoramidite (Compound 11, FIG. 2a)

SFPIM83

The compound 9 (200 mg, 0.352 mmol), predried over P$_2$O$_5$ for 18 h under vacuum, is dissolved in anhydrous CH$_2$Cl$_2$ (15 ml) and a solution of bis(N,N-diisopropylamino) benzyloxyphosphine (0.84M, 938 µl, 0.788 mmol, 2.24 eq) (compound 10) is added thereto. The reaction mixture is cooled to 0° C. and solid 1H-tetrazole (32 mg, 0.458 mmol, 1.3 eq) is added. After 1 h30 of stirring, the solvent is evaporated off under vacuum and the residue is purified by silica gel column chromatography (petroleum ether/ethyl acetate 9/1 containing 3% of Et$_3$N) so as to result in the compound 11 (259 mg, 92%) in the form of a colorless syrup.

$C_{45}H_{88}NO_6P$ (M=806.21 g/mol).

$^1$H NMR (250 MHz, CDCl$_2$) δ 0.88 (app t, 6H, 2CH$_2$), 1.16-1.30 (m, 60H, 24 CH$_2$, 4×CH$_2$ isopropyl), 1.60 (m, 4H, 2CH$_2$), 2.29 (t, 4H, 2CH$_2$, J=7.5 Hz), 3.55-3.85 (m, 4H, 2CH isopropyl, 2H3a), 4.17 (ddd, 1H, H1a$_B$, $J_{1aB-1aA}$=12 Hz, $J_{1B-2a}$=6.3 Hz, $J_{1aB-P}$=3 Hz), 4.34 (ddd, 1H, H1a$_A$, $J_{1aA-2a}=J_{1aA-P}$=4.5 Hz), 4.71 (m, 2H, CH$_2$Ph), 5.19 (m, 1H, H2a), 7.2-7.4 (m, 5H, 5CH$_{Ar}$).

3,4,5,6-Tetra-O-benzyl-1-O-(2,3,4,6-tetra-O-acetyl-α-D-mannopyranosyl)-2-O—[((S)-2,3-dipalmitoyloxypropyl)-(benzyl)phosphoryl]-D-myo-inositol (Compound 12, FIG. 2a)

SFPIM87

The compound 11 (259 mg, 0.321 mmol, 2.8 eq) and the compound 7 (100 mg, 0.115 mmol) are coevaporated together with anhydrous toluene (2×10 ml) and then dried for 30 min under a strong vacuum, before being dissolved, under an argon atmosphere, in anhydrous CH$_2$Cl$_2$ (12 ml). Solid 1H-tetrazole (26 mg, 0.368 mmol, 3.2 eq) is added at 0° C. and then, after 1 h30 of stirring at ambient temperature, the reaction mixture is cooled to −40° C. A solution of m-chloroperbenzoic acid (m-CPBA) (50%, 79 mg, 0.230 mmol, 2 eq) in CH$_2$Cl$_2$ (5 ml) is added dropwise. After 2 h of stirring while allowing the reaction medium to come back up to ambient temperature (approximately 20° C.), the reaction is stopped by adding an aqueous 10% of Na$_2$S$_2$O$_3$ solution (65 ml), and the mixture is extracted with diethyl ether (Et$_2$O) (130 ml). The organic phase is washed with an aqueous 5% solution of NaHCO$_3$ (3×65 ml) and then dried over MgSO$_4$. The solvent is evaporated off under vacuum and the residue is purified by silica gel column chromatography (4/1 petroleum ether/ethyl acetate), to give a fraction containing the first P-stereoisomer of the compound 12 (42 mg), a fraction containing a mixture of isomers (23 mg) and a fraction containing the second isomer of the compound 12 (38 mg) (overall yield 56%).

C$_{90}$H$_{127}$O$_{22}$P (M=1591.88 g/mol).

$^{13}$C NMR (100 MHz, CDCl$_3$) δ 173.36, 172.97, 170.72, 170.15, 169.89, 169.53, 138.36, 138.33, 137.90, 137.30, 136.00 (d), 135.67 (d), 128.82-172.08, 83.22, 81.12, 80.89, 78.75 (d), 76.11, 76.07, 76.01, 75.91, 72.99, 69.90, 69.82, 69.39, 69.33, 69.16, 67.45, 67.39, 65.91, 65.43, 62.89, 62.28, 34.33, 34.16, 32.06, 29.84, 29.79, 29.65, 29.50, 29.46, 29.28, 29.27, 24.98, 22.82, 20.96, 20.83, 20.74, 14.25.

3,4,5,6-Tetra-O-benzyl-1-O-α-D-mannopyranosyl-2-O—[((S)-2,3-dipalmitoyloxypropyl)(benzyl)phosphoryl]-D-myo-inositol (Compound 13, FIG. 2a)

SFPIM90

A freshly prepared 0.1 M sodium hydroxide solution (1 ml, 0.1 mmol, 4 eq) is added to a solution of compound 12 (40 mg, 0.025 mmol) in tetrahydrofuran (THF) (3 ml). The reaction mixture is stirred for 4 h at ambient temperature and is then diluted with CH$_2$Cl$_2$ (10 ml). The organic phase is washed with H$_2$O and then dried over MgSO$_4$. The solvent is evaporated off, so as to result in the expected compound 13 (36 mg, 100%). The NMR spectra of the crude product indicate the presence of approximately 30% of product still acetylated.

1-O-α-D-mannopyranosyl-2-O—[((S)-2,3-dipalmitoyloxy-propyl)phosphoryl]-D-myo-inositol (Compound 14, FIG. 2a)

SFPIM91

The compound 13 (36 mg, 0.025 mmol) obtained above is dissolved in a mixture of CH$_2$Cl$_2$/EtOH/acetic acid (4/5/0.5 ml). A large excess of palladium-on-carbon (Pd/C 10%) is added and the reaction is stirred for 6 h at ambient temperature (approximately 20° C.) under atmospheric hydrogen pressure (balloon). The catalyst is removed by a filtration through a millipore membrane and rinsed three times with 20 ml of CH$_2$Cl$_2$/EtOH mixture (1/1). The residual solvents are evaporated off under vacuum and coevaporated with toluene, so as to result in the compound 14 (25 mg, 100%) in the form of a white solid.

2) Preparation of Primary Cultures of Macrophages

Murine bone marrow cells were obtained from femurs of wild-type mouse lines. The cells obtained were cultured (10$^6$/ml) for 7 days in DMEM medium (Dulbecco's modified Eagle's medium) supplemented with 20% of horse serum and 30% of L929 cell-conditioned medium [22]. Three days after renewal of the medium, the cell preparation comprises a homogeneous population of macrophages.

3) Stimulation of the Macrophages of Wild-Type Mice with LPS in the Presence or in the Absence of PIM Isomer isoPIM$_1$-2C$_{16}$ (SFPIM91)

The macrophages derived from the bone marrow of wild-type mice were cultured on 96-well culture plates in the proportion of 10$^5$ cells per well, and were then stimulated with LPS (100 ng/ml, *Escherichia. coli*, serotype O111:B4, Sigma) with or without PIM analog (1-10 µg/ml). All the freeze-dried PIM analog preparations used are solubilized in DMSO and added to the cultures at a noncytotoxic maximum final concentration of 1%.

After stimulation for 24 hours, the culture supernatants were collected and analyzed for their content of TNF-α, IL-6, IL-12p40 and KC cytokines by ELISA (Duoset, R&D) and for their nitrite content by means of the Griess reaction.

Figure 3:
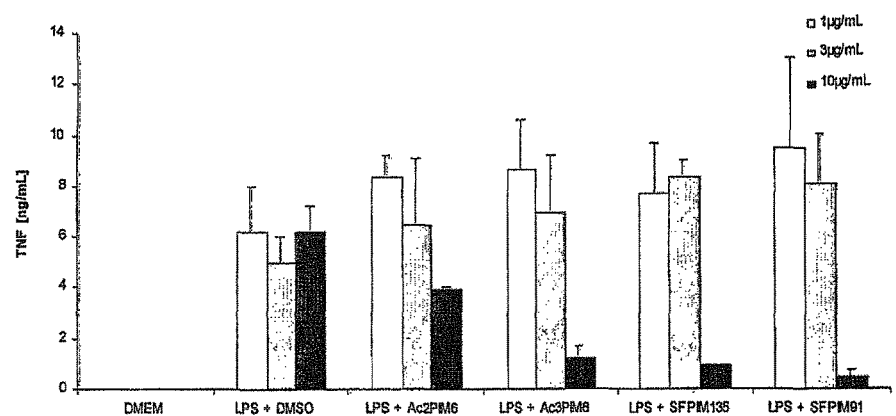
FIG. 3 represents the inhibition of TNF expression by primary macrophages stimulated with LPS in the presence of the "isomer" form of $PIM_1$, $isoPIM_1-2C_{16}$ (SFPIM91), in comparison with the natural PIMs $Ac2PIM_6$ and $Ac3PIM_6$, and the synthetic $PIM_1$ (SFPIM135) titrated at 1, 3 and 10 µg/ml.
Figure 4:
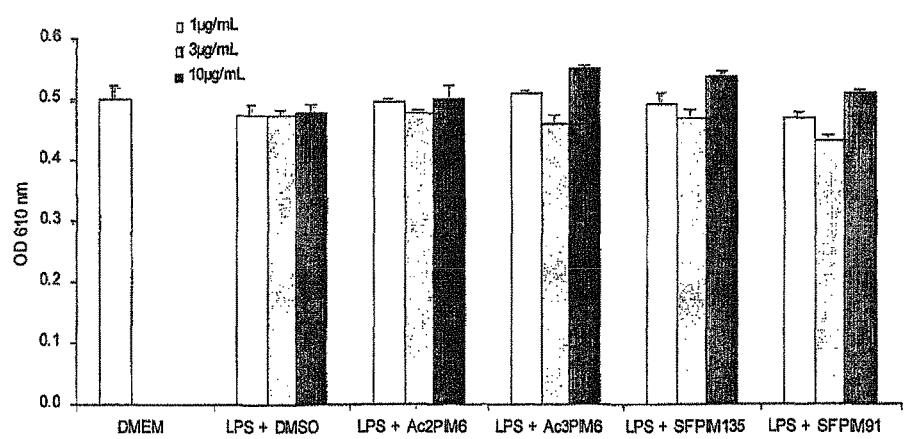
FIG. 4 represents the absence of cytotoxicity of $isoPIM_1$-$2C_{16}$ (SFPIM91), the natural PIMs $Ac2PIM_6$ and $Ac3PIM_6$, and the synthetic $PIM_1$ (SFPIM135), titrated at 1, 3 and 10 µg/ml.
Figure 5:
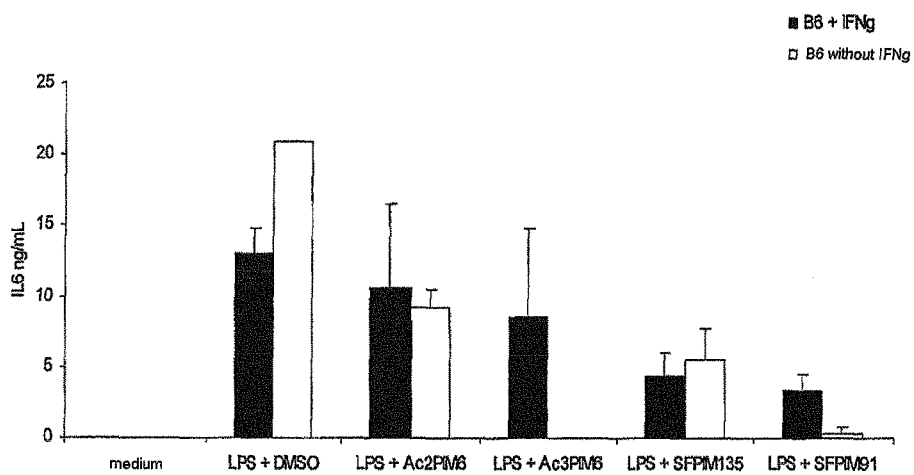
FIG. 5 represents the inhibition of IL-6 expression by primary macrophages stimulated with LPS, with or without IFNγ, in the presence of $isoPIM_1-2C_{16}$ (SFPIM91), in comparison with the natural PIMs $Ac2PIM_6$ and $Ac3PIM_6$, and the synthetic $PIM_1$ (SFPIM135), at 10 µg/ml.
Figure 6:
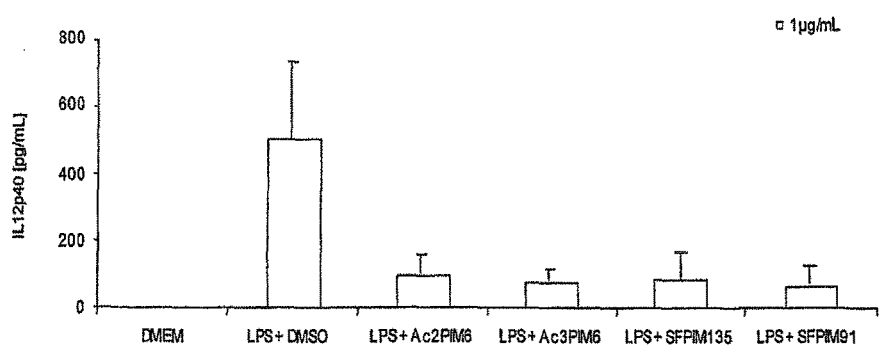
FIG. 6 represents the inhibition of IL-12 p40 expression by primary macrophages stimulated with LPS in the presence of $isoPIM_1-2C_{16}$ (SFPIM91), in comparison with the natural PIMs $Ac2PIM_6$ and $Ac3PIM_6$, and the synthetic $PIM_1$ (SFPIM135), at 1 µg/ml.
Figure 7:
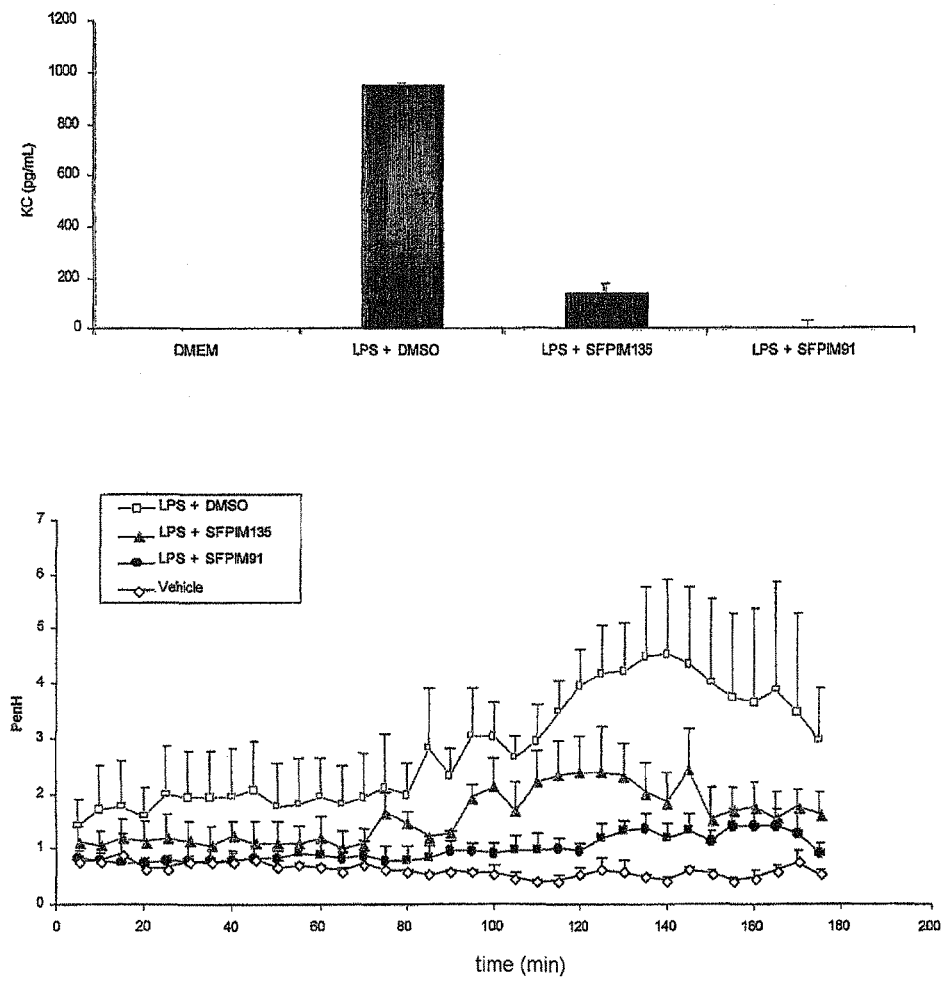
FIG. 7 represents the inhibition of KC expression by macrophages stimulated with LPS in the presence of synthetic $PIM_1$ (SFPIM135) and of $isoPIM_1-2C_{16}$ (SFPIM91), at 10 µg/ml.

The results show that the "isomer" form of PIM$_1$, isoPIM$_1$-2C$_{16}$ (SFPIM91), strongly inhibits the TNF-α synthesis induced in the LPS-stimulated macrophages, in comparison with the natural PIMs Ac2PIM$_6$ and Ac3PIM$_6$, and the synthetic PIM$_1$ (SFPIM135) (FIG. 3). Similar results were obtained for NO. An MTT cytotoxicity assay carried out on the same macrophages in the presence of the various PIM fractions made it possible to show the absence of cytotoxicity of the various preparations for the cells (FIG. 4). The expression of IL-6 by the macrophages stimulated with LPS in the presence or in the absence of interferon-γ is also inhibited (FIG. 5). The IL-12p40 secretion in response to the LPS is already strongly inhibited at concentrations of 1 µg/ml of PIM or of isoPIM (FIG. 6). Similarly, the production of chemokine KC, involved in the recruitment of inflammatory cells such as neutrophils, is also strongly reduced in the presence of PIM$_1$ (SFPIM135), or more strongly in the presence of isoPIM$_1$-2C$_{16}$ (SFPIM91) (FIG. 7).

Since preparations of PIM$_2$ and PIM$_6$ were initially identified as being stimulators of TNF secretion and IL-12p40 secretion by macrophage primary cultures, the PIM isomer preparations were tested for their ability to induce a pro-inflammatory response at concentrations up to 20 µg/ml. The results obtained showed no stimulation of the inflammatory response (TNF-α and IL-12p40) of the macrophage primary cultures, induced by the PIM isomer preparations.

4) In Vivo Anti-Inflammatory Activity of the Synthetic Derivatives of PIMs

In Vivo Model of Respiratory Distress

C57BL/6 mice received the vehicle alone (saline with 1.25% DMSO) or LPS (1 µg per mouse) from *Escherichia coli* (serotype O111:34; Sigma, St Louis, Mo., USA) in the absence or in the presence of PIM$_1$ (SFPIM135) or of isoPIM$_1$-2C$_{16}$ (SFPIM91) (50 µg/mouse), applied by nasal instillation in a volume of 40 µl under light anesthesia with ketamine-xylazine.

The resistance of the respiratory tracts was evaluated by noninvasive plethysmography over a period of 3 hours after the application of LPS. Awake mice were placed in plethysmography chambers (EMKA Technologies, Paris, France). The increase in respiratory pause (Penh), as measurement of respiratory discomfort, was recorded and analyzed using the Datanalyst Software (EMKA Technologies, Paris, France), and expressed as mean±SEM of Penh of n=2-3 individual mice per group [23].

Bronchoalveolar Lavage (BAL)

The BAL fluid is collected by canulating the trachea and washing the lungs four times with 0.5 ml of cold PBS. After centrifugation at 400×g for 10 min at 4° C., the supernatant from the first lavage is stored at −70° C. for the cytokine analysis. Pools of cell pellets are counted with Trypan blue (Sigma) in a hemocytometer cell. For differential counting, the cells are stained with Diff-Quik Staining (Merz & Dade AG., Dudingen, Switzerland). Two times one hundred cells are counted.

Cytokine Determination

The TNF and KC concentrations were evaluated by enzyme-linked immunosorbent assay (ELISA) in accordance with the instructions of the manufacturer (R&D Duoset, Minneapolis, Mo.).

Results

TNF is essential for LPS-induced acute respiratory dysfunction, as has been shown in TNF-deficient mice [23]. In order to determine the potential in vivo activity of PIM$_1$ (SFPIM135) and isoPIM$_1$-2C$_{16}$ (SFPIM91), they were tested for their inhibitory activity in a murine model of acute pulmonary inflammation and respiratory distress induced by intranasal application of LPS (1 µg/mouse).

Figure 11:
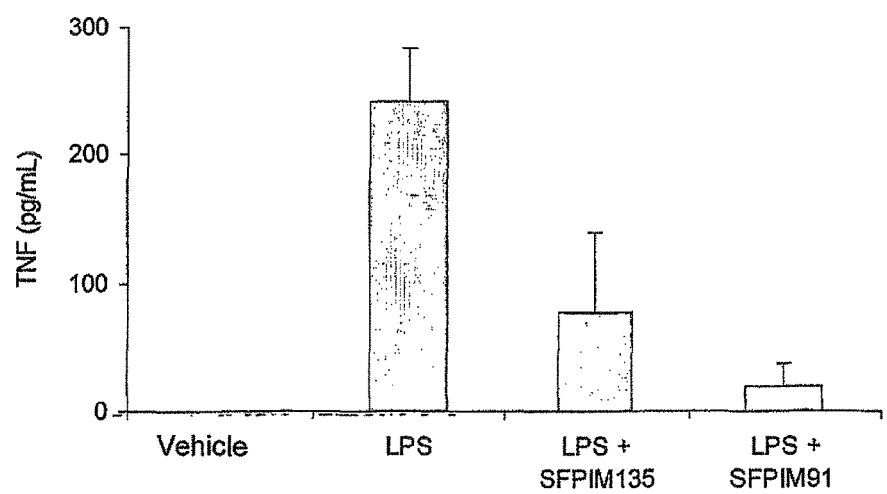
FIG. 11 represents the inhibition, by the synthetic $PIM_1$ (SFPIM135) and $isoPIM_1-2C_{16}$ (SFPIM91) of the secretion of TNF in the brochoalveolar lavage fluid in response to the endotoxin.

C57BL/6 mice received an intranasal application of 1 µg of LPS, and Penh was recorded for 200 minutes using noninvasive plethysmography. The graph of FIG. 11 represents the area under the curve (from 70 to 175 min). The values represent the mean±SEM of n=2-3 mice per group.

Figure 8:
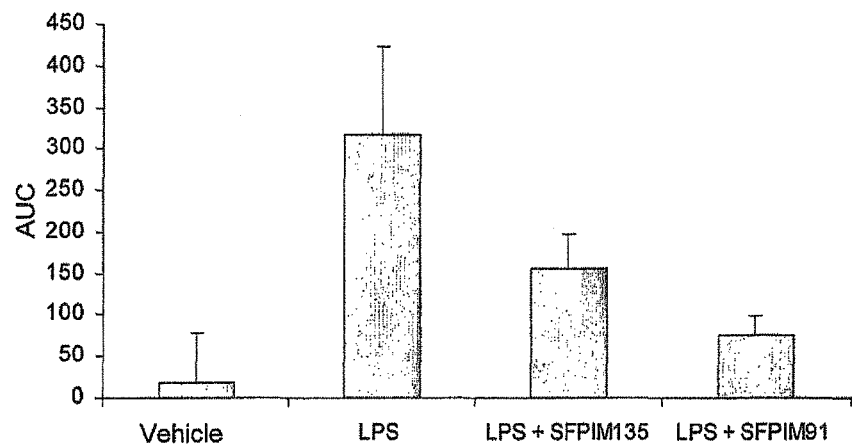
FIG. 8 represents the inhibition, by the synthetic $PIM_1$ (SFPIM135) and $isoPIM_1-2C_{16}$ (SFPIM91) of the response of the respiratory tracts to a local administration of endotoxin. The abbreviation "AUC" means area under the curve.

Typically, the mice receiving an intranasal application of LPS develop an acute increase in Penh (enhanced respiratory pause), which is a measurement of respiratory dysfunction, beginning 90 minutes after the application of LPS (FIG. 8). The addition of PIM$_1$ (SFPIM135) causes a partial reduction in the enhancement of Penh induced by LPS. This inhibition is even more pronounced after the addition of isoPIM$_1$-2C$_{16}$ (SFPIM91) (FIG. 8).

Figure 9:
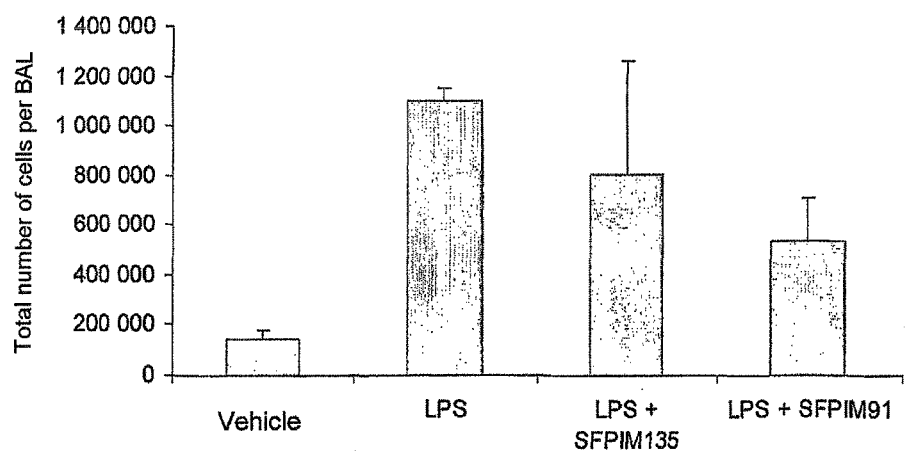
FIG. 9 represents the inhibition, by the synthetic $PIM_1$ (SFPIM135) and $isoPIM_1-2C_{16}$ (SFPIM91) of the recruitment of inflammatory cells, predominantly neturophils, into the bronchoalveolar space in response to the endotoxin.

LPS causes a recruitment of inflammatory cells in the respiratory tracts, measured as total number of cells in the bronchoalveolar fluid (BAL) of the mice treated with LPS. In this case, the number of inflammatory cells detected in the BAL 18 hours after the application of LPS is partially reduced in the presence of isoPIM$_1$-2C$_{16}$ (SFPIM91), and less so in the presence of PIM$_1$ (SFPIM135) (FIG. 9). Neutrophils constitute the majority of the inflammatory cells recruited after exposure to LPS. The macrophages are essentially unchanged. In this first experiment, a reduction in the number of neutrophils of up to 50% or 70% is observed in 2 mice out of 3 having received PIM$_1$ (SFPIM135) or isoPIM$_1$-2C$_{16}$ (SFPIM91), respectively.

Figure 10:
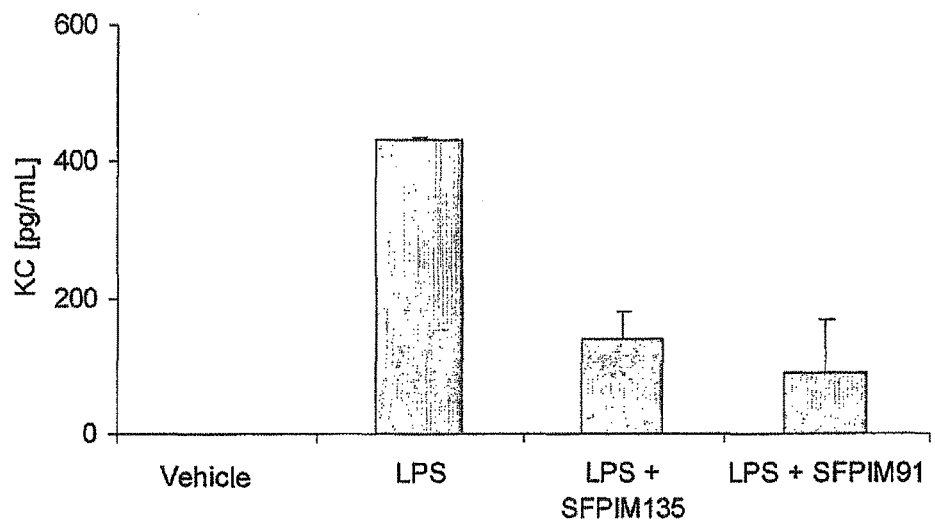
FIG. 10 represents the inhibition, by the synthetic $PIM_1$ (SFPIM135) and $isoPIM_1-2C_{16}$ (SFPIM91), of the secretion of chemokine KC, which participates in the recruitment of neurophils, in the bronchoalveolar lavage fluid in response to the endotoxin.

Neutrophil recruitment depends on various factors, including chemokine KC, even though it is not critically dependent on TNF [23]. In FIG. 10, the treated mice are sacrificed 24 hours after the intranasal application of 1 µg of LPS and the bronchoalveolar fluid is analyzed in order to determine the chemokine KC content. The secretion of KC in the bronchoalveolar space is greatly reduced by the coadministration of PIM$_1$ (SFPIM135) or isoPIM$_1$-2C$_{16}$ 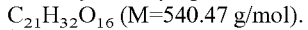91) (FIG. 10). Similarly, the release of TNF in the bronchoalveolar space is reduced by the coadministration of PIM$_1$ (SFPIM135) or more strongly by isoPIM$_1$-2C$_{16}$ (SFPIM91) (FIG. 11). The values represent the mean±SEM of n=3 mice per group, of a representative experiment of 3 independent experiments.

Additional experiments indicate that isoPIM$_1$-2C$_{16}$ (SFPIM91) causes a decrease in expression of several other inflammatory cytokines and chemokines in lungs exposed to endotoxins.

In these experiments, isoPIM$_1$-2C$_{16}$ (SFPIM91) causes a marked inhibition of pulmonary inflammation and of resistance of the respiratory tracts in response to local endotoxins.

Example 2

Figure 2B:
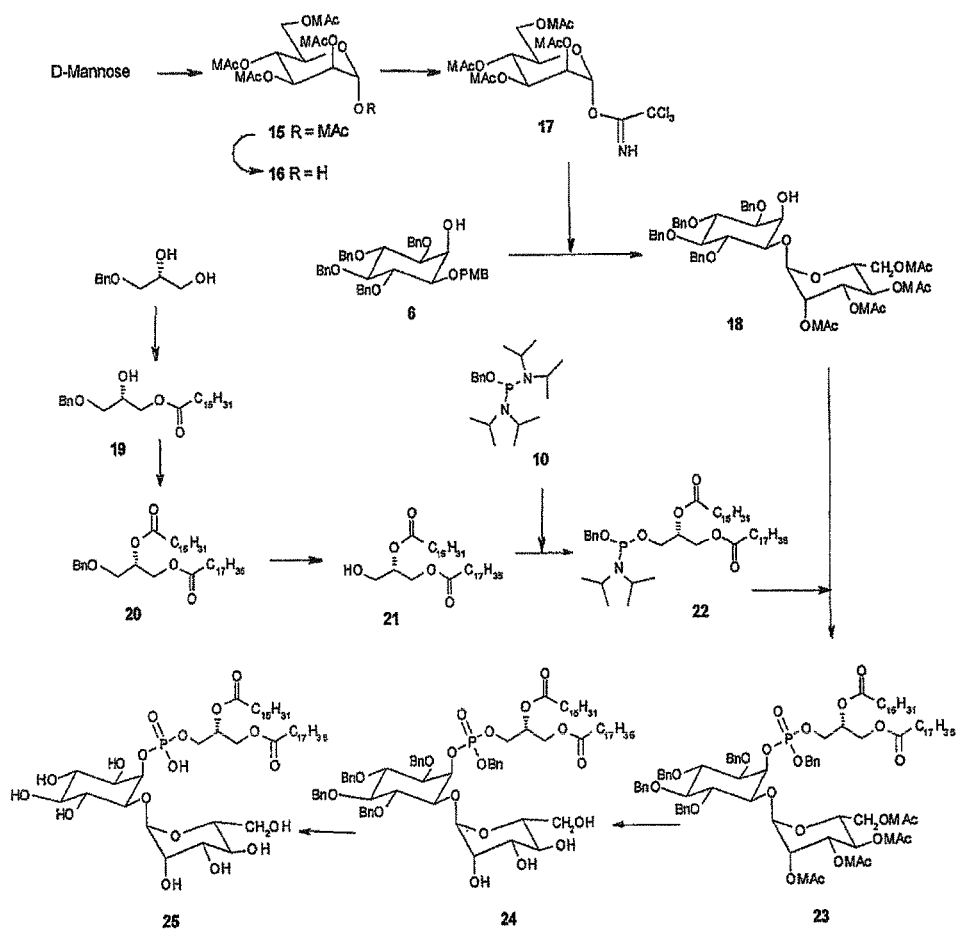

1) Synthesis of Compound 25 (IsoPIM1-C$_{16}$C$_{18}$) (FIG. 2b)

Per-O-methoxyacetyl-D-mannopyranose (Compound 15, FIG. 2b)

SFPIM-93

Methoxyacetyl chloride (600 µl, 7.22 mmol, 6.5 eq) is added dropwise to a solution of D-mannose (200 mg, 1.11 mmol) in pyridine (6 ml) at ambient temperature (approximately 20° C.), and the mixture is stirred for 18 h. The solvents are evaporated off and the residue is diluted in ethyl acetate (30 ml). The solution is then washed with a 1N aqueous HCl solution (10 ml) and then a saturated NaCl solution (10 ml), and dried over magnesium sulfate (MgSO$_4$). The solvents are evaporated off and purification by silica gel column chromatography (2/1 then 1/1 petroleum ether/ethyl acetate) results in the pure compound 15 (518 mg, 86%) in the form of a yellow syrup.

C$_{21}$H$_{32}$O$_{16}$ (M=540.47 g/mol).

$^1$H NMR (250 MHz, CDCl$_3$) δ 3.41 (s, 6H), 3.45 (s, 3H), 3.49 (s, 6H), 3.85-4.26 (m, 14H), 5.25-5.53 (m, 3H), 6.21 (s, 1H);

$^{13}$C NMR (62.9 MHz, CDCl$_3$) δ 59.34, 59.42, 59.50, 61.83, 65.50, 68.35, 68.82, 69.14, 69.26, 69.37, 70.44, 90.49, 167.61, 169.08, 169.22, 169.33, 169.90.

SI-MS: M calculated 540.17. found: 558.5 [M+NH$_4$]$^+$, 563.5 [M+Na]$^+$, 579.5 [M+K]$^+$.

2,3,4,6-Tetra-O-methoxyacetyl-D-mannopyranose (Compound 16, FIG. 2b)

SFPIM-114

Hydrazine acetate (500 mg, 5.48 mmol, 1.6 eq) is added to a solution of the compound 15 (1.850 g, 3.4 mmol) in dimethylformamide (DMF) (15 ml) cooled beforehand to −20° C. After 1 h of stirring at −20° C., the mixture is diluted with ethyl acetate (150 ml), and then washed with a saturated NaCl solution (5×50 ml), dried over MgSO$_4$ and concentrated under vacuum, to give the compound 16 (1.331 g, 83%) in the form of a yellow syrup.

C$_{18}$H$_{28}$O$_{14}$ (M=468.42 g/mol).

$^1$H NMR (400 MHz, CDCl$_3$) δ 3.34 (s, 3H), 3.35 (s, 3H), 3.39 (s, 3H), 3.41 (s, 3H) (4OMe), 3.87 (AB, 2H, CH$_2$OMe), 3.95 (s, 2H, CH$_2$OMe), 4.02 (s, 2H, CH$_2$OMe), 4.08 (AB, 2H, CH$_2$OMe), 4.2-4.35 (m, 3H, H5', H6'A, H6'B), 5.19 (d, 1H, H1', J$_{1-2}$=1.8 Hz), 5.27 (t, 1H, H4', J$_{4-3}$=10 Hz), 5.3 (dd, 1H, H2', J$_{2-3}$=3.2 Hz), 5.49 (dd, 1H, H3').

$^{13}$C NMR (100 MHz, CDCl$_3$) δ 59.45 (CH$_3$), 59.48 (CH$_3$), 59.50 (CH$_2$), 62.62 (C6'), 66.53 (CH$_2$, C4'), 68.00 (CH, C5'), 69.29 (CH, C3'), 69.34 (CH$_2$), 69.41 (CH$_2$), 69.49 (CH$_2$), 69.52 (CH$_2$), 70.50 (CH, C2'), 91.98 (CH, C1').

2,3,4,6-Tetra-O-methoxyacetyl-1-O-trichloroacetimidoyl-α-D-mannopyranose (Compound 17, FIG. 2b)

SFPIM-125

Trichloroacetonitrile (1.28 ml, 12.80 mmol, 12 eq) is added to a mixture of compound 16 (500 mg, 1.067 mmol) and 1,8-diazabicyclo[5.4.0]undec-7-ene (DBU) (45 µl, 0.299 mmol, 0.28 eq) in anhydrous dichloromethane (CH$_2$Cl$_2$) (10 ml) at ambient temperature (20° C.) under an argon atmosphere. After 10 min of stirring, the reaction mixture is purified by silica gel column chromatography (petroleum ether/ethyl acetate ½ containing 0.2% of triethylamine (Et$_3$N)) and thus results in the compound 17 (479 mg, 73%) in the form of a yellow syrup.

C$_{20}$H$_{28}$O$_{14}$NCl$_3$ (M=614.81 g/mol).

$^1$H NMR (250 MHz, CDCl$_3$) δ 3.41 (s, 3H, CH$_3$), 3.42 (s, 3H, CH$_2$), 3.45 (s, 3H, CH$_2$), 3.50 (s, 3H, CH$_2$), 3.95 (dd, 2H, CH$_2$OMe), 4.03 (s, 2H, CH$_2$OMe), 4.08 (s, 2H, CH$_2$OMe), 4.19 (dd, 2H, CH$_2$OMe), 4.22-4.33 (m, 2H, H5', H6'A), 4.40 (dd, 1H, J=5.3 and 13.3 Hz, H6'B), 5.45 (t, 1H, J=9.8 Hz, H4'), 5.55 (dd, 1H, J=5.2 and 10.0 Hz, H3'), 5.59 (dd, 1H, H2'), 6.32 (d, 1H, J=1.5 Hz, H1'), 8.84 (s, 1H, NH).

3,4,5,6-Tetra-O-benzyl-1-O-(2,3,4,6-tetramethoxyacetyl-α-D-mannopyranosyl)-D-myo-inositol (Compound 18, FIG. 2b)

SFPIM-207

The acceptor compound 6 (940 mg, 1.42 mmol, 1 eq) and the donor compound 17 (1.16 g, 1.89 mmol, 1.3 eq) are combined in the same round-bottomed flask and are placed under vacuum, over P$_2$O$_5$, for 18 h. The mixture is then placed under argon and 4 Å sieve is added thereto. The round-bottomed flask is left under an argon stream for 10 min, and then anhydrous CH$_2$Cl$_2$ (7 ml) is added. After stirring for a further 30 min under argon, the reaction medium is cooled to 0° C. and TMSOTf (68 µl, 0.38 mmol) is added dropwise. After stirring for 5 min at 0° C. and 1 h at ambient temperature (approximately 20° C.) under an argon atmosphere, the reaction mixture is cooled to 0° C. and the reaction is stopped by adding Et$_3$N (1 ml). The sieve is filtered off through sintered glass, the solvents are evaporated off under vacuum, and the residue is purified by silica gel column chromatography (1/1 petroleum ether/ethyl acetate) so as to result in the compound 18 (296 mg, 21%). (A fraction of 350 mg of the compound 18 as a mixture with the isomer initially expected, having lost the PMB but glycosylated at position 2 of the inositol, is also isolated).

C$_{52}$H$_{62}$O$_{19}$ (M=991.06 g/mol).

$^1$H NMR (400 MHz, CDCl$_3$) δ 2.89 (m, 1H, OH), 3.34 (s, 3H, CH$_3$), 3.41 (s, 3H, CH$_3$), 3.42 (s, 3H, CH$_3$), 3.44 (s, 3H, CH$_3$), 3.41-3.48 (m, 2H, 2CH$_{ins}$) 3.45 (dd, 1H, CH$_{ins}$, J=2.4, 6.0 Hz), 3.86-4.16 (m, 8H, 4CH$_2$OMe), 4.15 (dd, 1H, H6'A, J$_{6'A-5'}$=2.4 J$_{6'A-6'B}$=12 Hz), 4.29 (br s, 1H, H2), 4.34 (dd, 1H, H6'B, J$_{6'B-5'}$=4.8 Hz), 4.43 (ddd, 1H, H5'), 4.65-4.91 (m, 8H, 4CH$_2$Ph), 5.07 (d, 1H, H1', J$_{1'-2'}$=2 Hz), 5.31 (t, 1H, H4', J$_{4'-3'}$=J$_{4'-5'}$=10.0 Hz), 5.41 (dd, 1H, H2', J$_{2'-3'}$=3.2 Hz), 5.56 (dd, 1H, H3'), 7.15-7.4 (m, 20H, 4×5CH$_{Ar}$).

$^{13}$C NMR (62.9 MHz, CDCl$_3$) δ 59.42, 59.48, 59.52, 63.12 (C6'), 66.65 (4'), 68.83 (C5'), 69.26 (C2), 69.38 (C3'), 69.46 (2CH$_2$OMe), 69.49 (CH$_2$OMe), 69.74 (CH$_2$OMe), 69.87 (C2'), 73.17 (CH$_2$Ph), 76.0 (CH$_2$Ph), 76.03 (CH$_2$Ph), 76.28 (CH$_2$Ph), 80.27, 80.31, 81.15, 81.53 and 83.12 (CH$_{ins}$), 99.47 (C1'), 127.69-128.62 (11 peaks, CH$_{Ar}$), 137.88, 138.26, 138.57, 138.63, 169.25 (CO), 169.31 (CO), 169.49 (CO), 169.86 (CO).

3-O-benzyl-1-O-octadecanoyl-sn-glycerol (Compound 19, FIG. 2b)

SFPIM1

(Dimethylamino)pyridine (DMAP) (5.6 mg, 0.05 mmol, 0.1 eq) and then dicyclohexylcarbodiimide (DCC) (190 mg, 0.92 mmol, 2 eq) are added to a solution, cooled beforehand to 0° C., of stearic acid (130 mg, 0.46 mmol) and 3-O-benzyl-sn-glycerol (100 mg, 0.55 mmol, 1.2 eq) in anhydrous dichloromethane (CH$_2$Cl$_2$) (5 ml). The reaction mixture is stirred for 1 h at 0° C. and then 18 h at ambient temperature (approximately 20° C.) and is then filtered through cotton wool in order to remove part of the dicyclohexylurea formed. The solvent is evaporated off under vacuum and the residue is purified by silica gel column chromatography (6/1 petroleum ether/ethyl acetate) so as to result in the compound 19 (129 mg, 63%) in the form of a white solid. C$_{28}$H$_{48}$O$_4$ (M=448.69 g/mol).

$^1$H NMR (250 MHz, CDCl$_3$) δ 0.88 (t, 3H, CH$_3$, J=6.5 Hz), 1.25 (b, 28H, 14CH$_2$), 1.60 (m, 2H, 2H3"), 2.31 (t, 2H, 2H2", J=7.5 Hz), 2.64 (d, 1H, OH, J=3.5 Hz), 3.48 (dd, 1H, H3a$_A$, J$_{3aA-3aB}$=9.75 Hz, J$_{3aA-2a}$=6 Hz), 3.55 (dd, 1H, H3a$_B$, J$_{3aB-2a}$=4.5 Hz), 4.02 (m, 1H, H2a), 4.12 (dd, 1H, H1a$_A$, J$_{1aA-2a}$~4.8 Hz), 4.19 (dd, 1H, H1a$_B$, J$_{1aB-1aA}$=11.5 Hz, J$_{1aB-2a}$ 5 Hz), 4.55 (s, 2H, CH$_2$Ph), 7.33 (m, 5H, CH$_{Ar}$).

$^{13}$C NMR (62.9 MHz, CDCl$_3$) δ 14.22 (CH$_3$), 22.19 (CH$_2$), 25.00 (CH$_2$, C3"), 29.23, 29.36, 29.46, 29.66, 29.71, 29.76, 29.80 (7 CH$_2$), 32.02 (CH$_2$), 34.24 (CH$_2$, C2"), 65.43 (CH$_2$, C1a), 68.80 (CH, C2a), 71.00 (CH$_2$, C3a), 73.58 (CH$_2$Ph), 127.82 (CH$_{Ar}$), 127.94 (CH$_{Ar}$), 128.54 (CH$_{Ar}$), 137.77 (Cq$_{Ar}$), 174.01 (Cq, C1").

SI-MS: calculated 448.36. found: 449.5 [M+H]$^+$, 466.5 [M+NH$_4$]$^+$, 471.5 [M+Na]$^+$.

3-O-benzyl-2-O-hexadecanoyl-1-O-octadecanoyl-sn-glycerol (Compound 20, FIG. 2b)

SFPIM34

1-Ethyl-3-[3-(dimethylamino)propylcarbodiimide (EDCI) hydrochloride (662 mg, 3.45 mmol, 2.5 eq) and DMAP (34 mg, 0.28 mmol, 0.2 eq) are added to a solution of the compound 19 (620 mg, 1.38 mmol) and palmitic acid (708 mg, 2.76 mmol, 2 eq) in anhydrous CH$_2$Cl$_2$ (25 ml). The reaction mixture is stirred for 18 h at ambient temperature (approximately 20° C.) and then diluted with CH$_2$Cl$_2$ (100 ml). The organic phase is washed with a 1N HCl solution (40 ml), water (40 ml) and then a saturated NaCl solution (40 ml), and dried over MgSO$_4$. The solvent is evaporated off under vacuum and the residue is purified by silica gel column chromatography (25/1 then 20/1 petroleum ether/ethyl acetate) so as to result in the compound 20 (899 mg, 95%), in the form of a white solid.

C$_{44}$H$_{78}$O$_5$ (M=687.11 g/mol).

$^1$H NMR (250 MHz, CDCl$_3$) δ 0.88 (t, 3H, CH$_3$, J=6.5 Hz), 1.26 (m, 52H, 26CH$_2$), 1.60 (m, 4H, 2H3', 2H3"), 2.27 (t, 2H, J=7.5 Hz) and 2.31 (t, 2H, J=7.5 Hz) (2H2' and 2H2"), 3.59 (d, 2H, 2H3a, J=5 Hz), 4.19 (dd, 1H, H1a$_A$, J$_{1aA-1aB}$=11.75 Hz, J$_{1A-2a}$=6.3 Hz), 4.35 (dd, 1H, H1a$_B$, J$_{1aB-2a}$=3.8 Hz), 4.53 (AB, 2H, CH$_2$Ph, J=12.2 Hz), 5.24 (quint., 1H, H2a), 7.32 (m, 5H, CH$_{Ar}$).

NMR (100 MHz, CDCl$_3$) δ 14.23 (CH$_3$), 22.82 (CH$_2$), 25.01 and 25.08 (2CH$_2$, C3', C3"), 29.22-29.83 (CH$_2$, 8 lines), 32.06 (CH$_2$), 34.23 and 34.44 (2CH$_2$), 62.16 (CH2, C1a), 68.38 (CH$_2$, C3a), 70.12 (CH, C2a), 73.42 (CH$_2$Ph), 127.72 (CH$_{Ar}$), 127.87 (CH$_{Ar}$), 128.51 (CH$_{Ar}$) 137.83 (Cq$_{Ar}$), 173.16 (Cq, CO), 173.45 (Cq, CO).

SI-MS: M calculated 686.58. found: 687.5 [M+H]$^+$, 704.5 [M+NH$_4$]$^+$, 709.5 [M+Na]$^+$.

2-O-hexadecanoyl-1-O-octadecanoyl-sn-glycerol (Compound 21, FIG. 2b)

SFPIM29

The compound 20 (250 mg, 0.36 mmol) is dissolved in a CH$_2$Cl$_2$/EtOH mixture (1/2.5, 14 ml). A large excess of palladium-on-carbon (Pd/C 10%) is added and the reaction is stirred for 4 h at ambient temperature (approximately 20° C.) under atmospheric hydrogen pressure (balloon). The reaction mixture is heated to 30° C. for better dissolution of the expected product and the catalyst is removed by filtration through a millipore membrane. It is rinsed 3 times with 20 ml of CH$_2$Cl$_2$/EtOH mixture (1/1) preheated to 30° C. The residual solvents are evaporated off under vacuum so as to result in the expected compound 21 (215 mg, 99%) in the form of a white solid.

C$_{37}$H$_{72}$O$_5$ (M=596.98 g/mol).

$^1$H NMR (250 MHz, CDCl$_3$) δ 0.88 (t, 6H, 2CH$_3$), 1.26 (m, 52H, 26CH$_2$), 1.62 (m, 4H), 1.99 (very broad s, 1H, OH), 2.32 (t, 2H, J=7.7 Hz), 2.34 (t, 2H, J=7.5 Hz), 3.73 (d, 2H, 2H3a, J=5 Hz), 4.23 (dd, 1H, H1a$_A$, J$_{1aA-1aB}$=11.75 Hz, J$_{1A-2a}$=5.75 Hz), 4.35 (dd, 1H, H1a$_B$, J$_{1aB-2a}$=4.5 Hz), 5.08 (quint., 1H, H2a, J=4.5 Hz).

$^{13}$C NMR (62.9 MHz, CDCl$_3$) δ 14.27 (CH$_3$), 22.84 (CH$_2$), 25.04 and 25.09 (2CH$_2$), 29.25-29.85 (CH$_2$, 8 lines), 32.08 (CH$_2$), 34.26 and 34.44 (2CH$_2$), 61.68, 62.16, 72.25, 173.57 (Cq, CO), 173.93 (Cq, CO).

(S)-2-O-hexadecanoyloxy-1-O-octadecanoyloxypropyl benzyl (N,N-diisopropylamino)phosphoramidite (Compound 22, FIG. 2b)

SFPIM47

Solid 1H-tetrazole (11 mg, 0.151 mmol, 0.6 eq) and the compound 21 (150 mg, 0.251 mmol) are separately dried under vacuum over P$_2$O$_5$ for 1 h before being combined and dissolved in anhydrous CH$_2$Cl$_2$ (2 ml). The stock solution of compound 10 (0.84M, 358 μl, 0.301 mmol, 1.2 eq) is added and, after 30 min of stirring at ambient temperature (approximately 20° C.), the reaction mixture is diluted with CH$_2$Cl$_2$ (50 ml), and cooled to 0° C., and the organic phase is washed with a saturated solution of NaHCO$_3$ at 0° C. (10 ml), and then dried over MgSO$_4$. The solvent is evaporated off and rapid purification on a silica gel chromatography column (petroleum ether/ethyl acetate 6/1 containing 1% Et$_3$N) makes it possible to obtain the expected compound 22 (100 mg, 48%) in the form of a colorless oil.

C$_{50}$H$_{92}$NO$_6$P (M=834.27 g/mol).

$^1$H NMR (400 MHz, CDCl$_3$) δ 0.88 (t, 6H, 2CH$_3$), 1.18 (d, 6H, CH$_3$ isopropyl), 1.19 (d, 6H, CH$_3$ isopropyl), 1.25 (m, 52H, 26 CH$_2$), 1.60 (m, 4H, 2CH$_2$), 2.29 (2t, 4H, 2CH$_2$), 3.56-3.9 (2 m, 4H, 2CHMe$_2$, 2H3a), 4.17 (ddd, 1H, H1a$_B$, J=4.8, 6.4 and 12 Hz), 4.34 (ddd, 1H, H1a$_A$, J=4, 8 and 12 Hz), 4.65 and 4.66 (2 dd, 1H, POCH$_A$Ph, J$_{A,B}$=12.4 Hz, J$_{A,P}$=8.4 Hz), 4.732 and 4.735 (2 dd, 1H, POCH$_B$Ph, J$_{A,B}$=12.4 Hz, J$_{A,P}$=8.4 Hz), 5.19 (m, 1H, H2a), 7.3-7.4 (m, 5H, 5CH$_{Ar}$).

$^{31}$P NMR (162 MHz, CDCl$_3$) δ 148.70, 148.80.

3,4,5,6-Tetra-O-benzyl-1-O-(2,3,4,6-tetra-O-methoxyacetyl-α-D-mannopyranosyl)-2-O-MS)-2-O-hexadecanoyl-3-O-octadecanoylpropyl)(benzyl) phosphoryl)-D-myo-inositol (Compound 23, FIG. 2b)

SFPIM214

The compound 22 (290 mg, 0.348 mmol, 3 eq) and the compound 18 (115 mg, 0.116 mmol) are coevaporated together with anhydrous toluene (2×10 ml) and then dried for 30 min under a strong vacuum before being dissolved, under an argon atmosphere, in anhydrous CH$_2$Cl$_2$ (8 ml). Solid 1H-tetrazole (41 mg, 0.58 mmol, 5 eq) is added at 0° C. and then, after 1 h30 of stirring at ambient temperature, the reaction mixture is cooled to −40° C. A solution of m-chloroperbenzoic acid (m-CPBA) (50%, 120 mg, 0.348 mmol, 3 eq) in CH$_2$Cl$_2$ (8 ml) is added dropwise. After 2 h of stirring while allowing the reaction medium to return to ambient temperature (approximately 20° C.), the reaction is stopped by adding an aqueous 10% Na$_2$S$_2$O$_3$ solution (50 ml), and the mixture is extracted with diethyl ether (Et$_2$O) (100 ml). The organic phase is washed with an aqueous 5% NaHCO$_3$ solution (3×50 ml) and then dried over MgSO$_4$. The solvent is evaporated off under vacuum and the residue is purified by silica gel column chromatography (petroleum ether/ethyl acetate 2/1 with a gradient up to 1/1), to give a fraction containing a first P-stereoisomer of the compound 23 (55 mg) and a fraction containing a mixture of isomers (76 mg containing approximately 30% of the first isomer) (overall yield 65%).

C$_{96}$H$_{139}$O$_{26}$P (M=1740.14 g/mol).

SI-MS m/z M calculated: 1738.92. found: 1740.5 [M+H]$^+$, 1763.5 [M+Na]$^+$.

HRMS calculated for [M+H]$^+$: C$_{96}$H$_{140}$O$_{26}$P: 1739.9370. found: 1739.9386.

3,4,5,6-Tetra-O-benzyl-1-O-α-D-mannopyranosyl-2-O—[((S)-2-O-hexadecanoyl-3-O-octadecanoylpropyl)(benzyl)-phosphoryl)-D-myo-inositol (Compound 24, FIG. 2b)

SFPIM218

The compound 23 (129 mg, 0.074 mmol) is dissolved in a mixture of CHCl$_3$/MeOH (4/1, 1 ml). The reaction mixture is cooled to 0° C. and t-butylamine (160 μl) is added thereto. After 10 min of stirring at 0° C. and then 1 h while allowing the reaction medium to return to ambient temperature, the solvents are evaporated off under a strong vacuum at ambient temperature (approximately 20° C.) and the residue is purified using two successive silica gel chromatography columns (20/1 CH$_2$Cl$_2$/MeOH) with a large amount of silica, to give the expected compound 24 (67 mg, 63%) in the form of a homogeneous white solid (NMR: presence of the two P*-stereoisomers).

C$_{84}$H$_{123}$O$_{18}$P (M=1415.85 g/mol).

HRMS calculated for [M+H]$^+$: C$_{84}$H$_{124}$O$_{18}$P: 1451.8525. found: 1451.8521.

1-O-α-D-mannopyranosyl-2-O—[((S)-2-O-hexadecanoyl-3-O-octadecanoylpropyl)phosphoryl]-D-myo-inositol (Compound 25, FIG. 2b)

SFPIM219

The compound 24 (63 mg, 0.043 mmol) is dissolved in a mixture of CH$_2$Cl$_2$/EtOH (0.6/1, 16 ml). A large excess of palladium-on-carbon (Pd/C 10%) is added and the reaction is stirred for 18 h at ambient temperature (approximately 20° C.) under atmospheric hydrogen pressure (balloon). The catalyst is removed by a filtration through a millipore membrane and rinsed 3 times with a CH$_2$Cl$_2$/EtOH mixture (1/1) (20 ml). The residual solvents are evaporated off under vacuum, so as to result in the compound 25 (43 mg, 100%) in the form of a very homogeneous white solid (NMR).

C$_{49}$H$_{93}$O$_{18}$P (M=1001.25 g/mol).

$^1$H NMR (400 MHz, CD$_3$OD/CDCl$_3$ 0.7/0.3 ml) δ 0.88 (t, 6H, 2CH$_3$), 1.26 (m, 52H, 26 CH$_2$), 1.60 (m, 4H), 2.32 (t, 2H, J=7.6 Hz), 2.35 (t, 2H, J=7.6 Hz), 3.22 (t, 1H, H5, J$_{4-5}$=J$_{5-6}$=8.8 Hz), 3.52 (br d, 1H, H3), 3.55 (t, 1H, H4', J$_{4'-5'}$=10.0 Hz), 3.56 (t, 1H, H4, J$_{4-3}$=8.8 Hz), 3.66 (m, 1H, H1), 3.67-3.72 (m, 2H, H6, H6'A), 3.81 (dd, 1H, H3', J$_{3'-4'}$=9.4, J$_{3'-2'}$=3.2 Hz), 3.83 (m, 1H, H5'), 3.89 (dd, 1H, H6'B, J$_{6'B-5'}$=2, J$_{6'B-6'A}$=11.6 Hz), 3.97 (dd, 1H, H2', J$_{2'-1'}$=1.6 Hz), 4.16-4.23 (m, 3H, H3aA and 2H1a), 4.42 (dd, 1H, H3aB, J$_{3aB-2aa}$=3.2, J$_{3aB-3aA}$=12 Hz), 4.75 (ddd, 1H, H2, J$_{2-3}$~10, J$_{2-1}$=2.2 Hz), 5.16 (d, 1H, H1', J=1.2 Hz), 5.26 (m, 1H, H2a).

$^{13}$C NMR (100 MHz, CD$_3$OD/CDCl$_3$ 0.7/0.3 ml) δ 14.40 (CH$_3$), 23.43, 25.67, 25.70, 29.90, 29.93, 30.15, 30.16, 30.33, 30.36, 30.44, 30.46, 30.48, 32.74, 34.75, 34.88, 62.83 (C6'), 63.23 (C3a), 65.87 (d, C1a), 68.77 (C4'), 70.89 (d, C2a), 71.48 (C3 and C2'), 73.58 (C4), 73.96 (C6), 74.70 (C5'), 75.79 (C5), 76.37 (d, C1), 81.37 (d, C1), 102.95 (C1'), 174.43 (C0), 174.81 (C0).

$^{31}$P NMR (162 MHz, CD$_3$OD/CDCl$_3$ 0.7/0.3 ml) δ −1.71 ppm. HRMS calculated for [M+H]$^+$: C$_{49}$H$_{94}$O$_{18}$P: 1001.6178. found: 1001.6172.

2) Stimulation of Wild-Type Mouse Macrophages with LPS in the Presence of PIM$_1$ Isomer isoPIM$_1$-C$_{16}$C$_{18}$ (SFPIM219)

Figure 12:
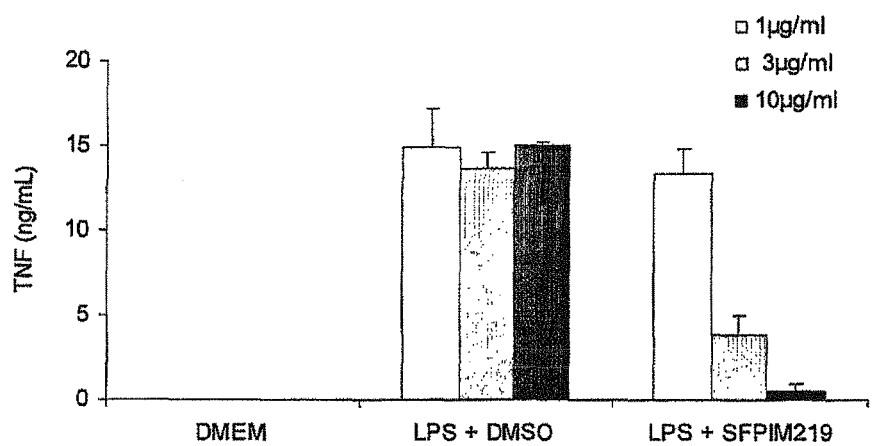
FIG. 12 represents the inhibition of the TNF expression by primary macrophages stimulated with LPS in the presence of the "isomer" form of $PIM_1$, $isoPIM_1-C_{16}C_{18}$ (SFPIM219), titrated at 1, 3 and 10 µg/ml.

A novel PIM isomer, isoPIM$_1$C$_{16}$C$_{18}$ (SFPIM219), was tested for its inhibitory activity on LPS-stimulated macrophages (FIG. 12).

The macrophages derived from the bone marrow of wild-type mice were cultured on 96-well culture plates in a proportion of 10$^5$ cells per well, and then stimulated with LPS (100 ng/ml, Escherichia coli, serotype O111:54, Sigma) with isoPIM$_1$C$_{16}$C$_{18}$ (SFPIM219) (1-10 μg/ml) or a DMSO control. The preparation of freeze-dried SFPIM219 which is used is solubilized in DMSO and added to the cultures at a noncytotoxic maximum final concentration of 1%.

After stimulation for 24 hours, the culture supernatents were collected and analyzed for their content of cytokines TNF-α or IL-12p40 by ELISA (R&D Duoset, Minneapolis, Mo.). The results correspond to the mean±SD of n=2 mice per genotype.

Figure 13:
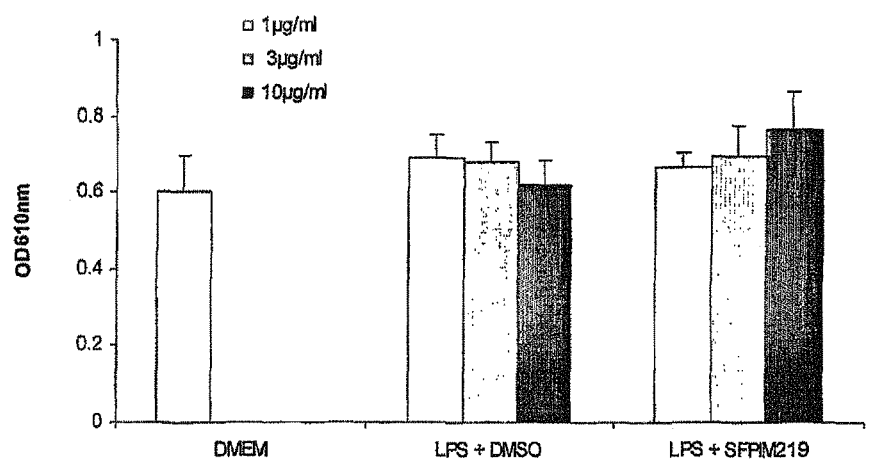
FIG. 13 represents the absence of cytotoxicity of $isoPIM_1$-$C_{16}C_{18}$ (SFPIM219), titrated at 1, 3 and 10 µg/ml.

The isoPIM$_1$C$_{16}$C$_{18}$ (SFPIM219) strongly inhibits TNF secretion (FIG. 12). An MTT cytotoxicity assay carried out on the same macrophages incubated in the presence of isoPIM$_1$C$_{16}$C$_{18}$ (SFPIM219) made it possible to show its lack of cytotoxicity on macrophages (FIG. 13).

Figure 14:
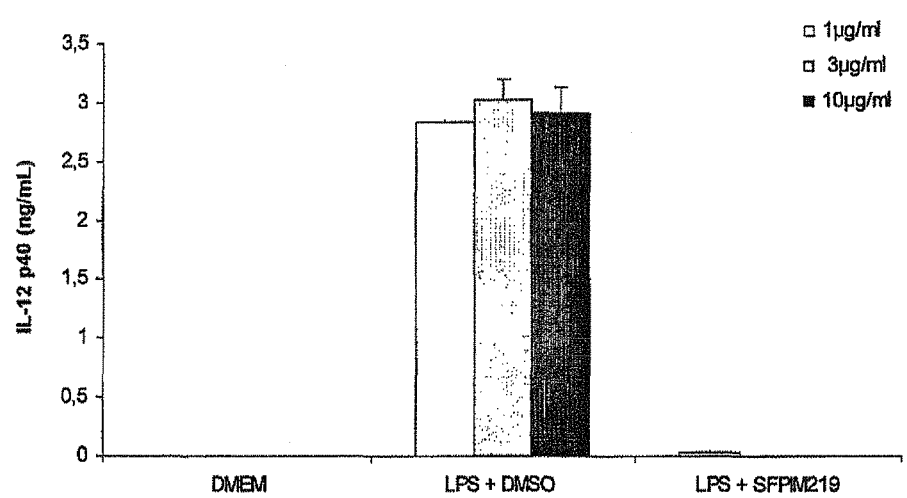
FIG. 14 represents the inhibition of IL-12 p40 expression by primary macrophages stimulated with LPS in the presence of the "isomer" form of $PIM_1$, $isoPIM_1-C_{16}C_{18}$ (SFPIM219), titrated at 1, 3 and 10 µg/ml.

The IL-12p40 secretion in response to LPS is already greatly inhibited at concentrations of 1 μg/ml of isoPIM$_1$C$_{16}$C$_{18}$ (SFPIM219) (FIG. 14).

Examples 3 and 4

1) Example 3

Figure 2C:
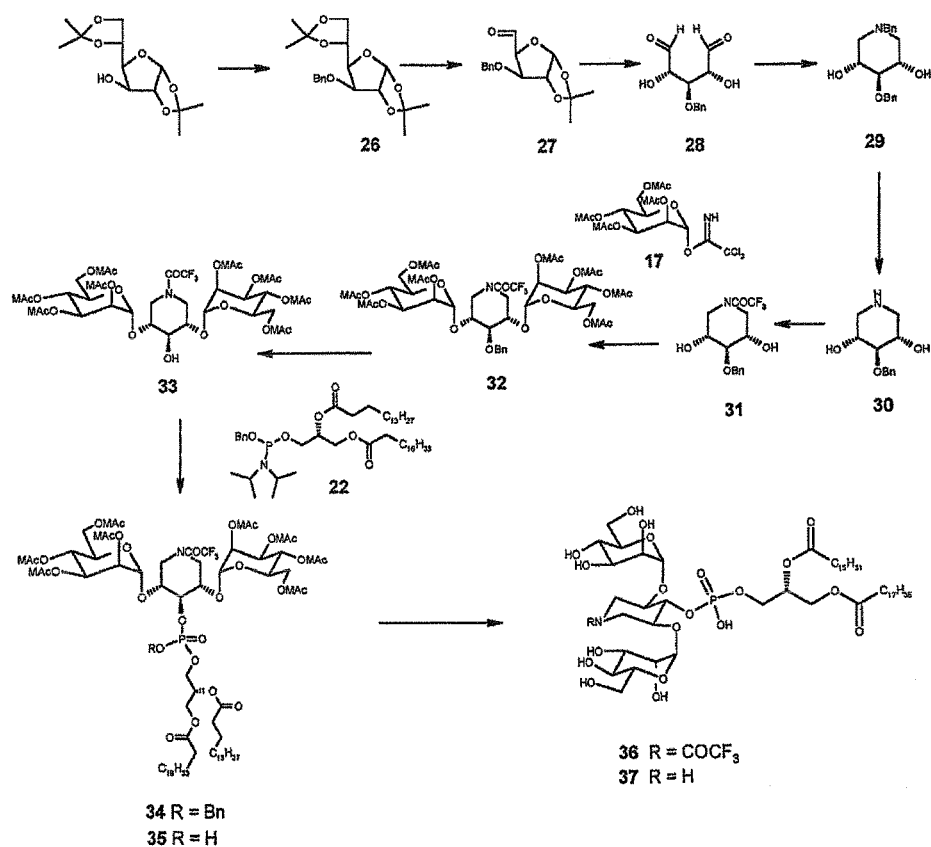

Synthesis of Compound 36 of FIG. 2c or PIM-2-mimNCOCF$_3$

SFPIM324-t2

Example 4

Synthesis of Compound 37 of FIG. 2c or PIM-2mimNH

SFPIM324-t8

3-O-benzyl-1,2:5,6-di-O-isopropylidene-α-D-glucofuranose (Compound 26, FIG. 2c)

SFPIM311

Sodium hydride (in the form of a dispersion at 60% in mineral oil) (2.5 g; 62 mmol; 1.2 eq.) is added at 0° C., under a nitrogen atmosphere, to a solution of commercial 1,2:5,6-di-O-isopropylidene-α-D-glucofuranose (13.5 g; 52 mmol) in anhydrous THF (100 ml). The mixture is stirred for 20 minutes at 0° C. After the addition, at ambient temperature (approximately 20° C.) of tetrabutylammonium iodide (149 mg; 0.4 mmol; 0.008 eq.), benzyl bromide (9 ml; 76 mmol; 1.3 eq.) is added dropwise. The mixture is refluxed for 2 h, and then methanol (10 ml) is added slowly. The mixture is diluted with dichloromethane (100 ml) and water (40 ml). The aqueous phase is extracted 3 times with dichloromethane (50 ml). The organic phases are combined, dried, and concentrated under vacuum. The crude product is purified by silica gel chromatography (cyclohexane/Et$_2$O 4/1+0.4% of Et$_3$N), to give the compound 26 in the form of a yellow oil.

C$_{19}$H$_{26}$O$_6$ (M=350.42 g/mol).

$^1$H NMR (400 MHz, CDCl$_3$): δ 1.31 (s, 3H, CH$_3$), 1.37 (s, 3H, CH$_3$), 1.43 (s, 3H, CH$_3$), 1.49 (s, 3H, CH$_3$), 4.00 (d, 1H, H6A, J$_{6A-5}$=5.6, J$_{6A-6B}$=8.4 Hz), 4.02 (d, 1H, H3, J$_{4-3}$=3.0 Hz), 4.11 (d, 1H, H6B, J$_{6B-5}$=6.0 Hz), 4.15 (d, 1H, H4, J$_{4-5}$=7.6 Hz), 4.37 (m, 1H, H5), 4.58 (d, 1H, H2, J$_{2-1}$=3.6 Hz), 4.66 (AB, 2H, CH$_2$Ph), 5.90 (d, 1H, H1), 7.27.35 (m, 5H, CHar).

$^{13}$C NMR (101 MHz, CDCl$_3$): δ 25.57 (CH$_3$), 26.37 (CH$_3$), 26.92 (CH$_3$), 26.97 (CH$_3$), 67.53 (C6'), 72.50 (CH$_2$Ph), 72.65 (C5'), 81.45 (CV), 81.83 (C3'), 82.79 (C2'), 105.42 (C1'), 109.10 (Cq), 111.90 (Cq), 127.77, 127.96, 128.52, 137.77.

SI-MS m/z M calculated: 350.17. found: 351.0 [M+H]$^+$, 373.0 [M+Na]$^+$.

3-O-benzyl-1,2-O-isopropylidene-α-D-xylopentodialdo-1,4-furanose (Compound 27, FIG. 2c)

SFPIM268A

The compound 27 is synthesized according to [25]. A solution of 26 (1.03 g; 2.9 mmol) in an acetic acid/water mixture (21/9 ml) is stirred at 45° C. for 2 hours. The reaction medium is then cooled to 0° C., and a solution of sodium periodate (692 mg; 3.23 mmol; 1.1 eq.) in water (7 ml) is added. The medium is stirred at ambient temperature (approximately 20° C.) for approximately 18 h. Dichloromethane (15 ml) is added and the aqueous phase is extracted 3 times with dichloromethane (15 ml). The organic phases are combined, and then washed twice with water (20 ml), dried over MgSO$_4$ and concentrated under vacuum. The residue is coevaporated twice with toluene. The aldehyde 27 is used without purification, in the next step.

$^1$H NMR (250 MHz, CDCl$_3$): δ 1.33 (s, 3H, CH$_3$), 1.47 (s, 3H, CH$_3$), 4.33 (d, 1H, H3, J$_{3-1}$=3.7 Hz), 4.54 (AB, 2H, CH$_2$Ph), 4.61 (dd, 1H, H4, J$_{4-5}$=1.5, J$_{4-3}$=3.7 Hz), 4.64 (d, 1H, H2, J$_{2-1}$=3.7 Hz), 6.12 (d, 1H, H1), 7.1-7.4 (m, 5H, CHar), 9.67 (d, 1H, H5, J$_{5-4}$=1.8 Hz).

3-O-benzylxylopentodialdo-1,4-furanose (Compound 28, FIG. 2c)

SFPIM268

Dowex 50WX8 resin (3.4 g) is added to a solution of 27 (2.9 mmol) in a dioxane/water mixture (10/4 ml). The medium is stirred gently for 18 h at 75° C. The resin is filtered off through sintered glass and rinsed with a dioxane/water mixture. The solvents are evaporated off under reduced pressure. The residue is coevaporated several times with toluene until the product 28 is obtained in the form of an orangey-red foam. It is used without purification, in the next step.

N-benzyl-3-O-benzyl-1,5-dideoxy-1,5-iminoxylitol (Compound 29, FIG. 2c)

SFPIM272

Sodium cyanoborohydride (554 mg, 2.67 mmol, 3 eq.) is added, under a nitrogen atmosphere, to a solution of 28 (700 mg, 2.9 mmol), previously dried over P$_2$O$_5$ overnight, in anhydrous methanol (50 ml). The mixture is stirred in the presence of 3 Å molecular sieve for 10 minutes. The medium is cooled to −78° C., and then glacial acetic acid (332 µl, 5.8 mmol, 2 eq.) and benzylamine (292 µl, 2.67 mmol, 0.9 eq.) are added. After returning to ambient temperature (approximately 20° C.), the medium is stirred for 18 h and then filtered through celite. The celite is rinsed with ethyl acetate (3×10 ml). The solvents are evaporated under reduced pressure. The residue is taken up in ethyl acetate (60 ml) and washed with a saturated solution of NaHCO$_3$ (20 ml) and then twice with water (20 ml). The organic phase is dried, and then concentrated under vacuum, to give the compound 29 in the form of a homogeneous white solid. The compound can optionally be recrystallized from ethyl acetate.

C$_{19}$H$_{23}$O$_3$N (M=313.40 g/mol).

$^1$H NMR (250 MHz, CDCl$_3$): δ 2.24 (dd, 2H, H1aA, H5a'A, J$_{1aA-2a}$=J$_{5aA-4a}$=8, J$_{1aA-1aB}$=J$_{5aA-5aB}$=11 Hz), 2.45 (m, 2H, OH), 2.85 (dd, 2H, H1aB, H5aB, J$_{1aB-2a}$=J$_{5aB-4a}$=3.5 Hz), 2.25 (app t, 1H, H3a, J$_{2a-3a}$=J$_{3a-4a}$=7 Hz), 3.55 (s, 2H, CH$_2$Ph), 3.77 (ddd, 2H, H4a, H2a), 4.76 (s, 2H, CH$_2$Ph), 7.20-7.40 (m, 10H, 2×5 CHar).

$^{13}$C NMR (101 MHz, CDCl$_2$): δ 57.12 (C1a, C5a), 62.20 (CH$_2$Ph NBn), 69.91 (C2a, C4a), 73.98 (CH$_2$Ph OBn), 84.30 (C3a, signal of weak intensity), 127.39-129.14 (9 peaks, CHar), 137.86 (Cqar), 138.68 (Cgar).

SI-MS m/z M calculated: 313.17. found: 314.0 [M+H]$^+$, 336.0 [M+Na]$^+$.

3-O-benzyl-1,5-dideoxy-1,5-iminoxylitol (Compound 30, FIG. 2c)

SFPIM314

The compound 29 (300 mg; 0.957 mmol) is dissolved in EtOH (10 ml). An excess of palladium hydroxide 20% on carbon is added and the reaction medium is stirred at ambient temperature (approximately 20° C.) under atmospheric hydrogen pressure for 20 h. Palladium hydroxide 20% on carbon is again added and the reaction is continued for a further 18 h. The reaction medium is filtered through milli- pore membranes, and the catalyst is rinsed with EtOH (2×10 ml). The filtrate is evaporated under reduced pressure, so as to result in the compound 30 (172 mg, approximately 35% of O-debenzylated product is observed).

C$_{12}$H$_{17}$NO$_3$ (M=223.27 g/mol).

$^1$H NMR (400 MHz, CD$_3$OD): (contains 35% of O-debenzylated compound mentioned above*) δ *2.38 (dd, ~0.4H, *H1aA, *H5aA, J$_{1aA-2a}$=J$_{5aA-4a}$=10.1, J$_{1aA-1aB}$=J$_{5aA-5aB}$=12.6 Hz), 2.45 (dd, ~1.7H, H1aA, H5aA, J$_{1aA-2a}$=J$_{5aA-4a}$=9.7, J$_{1aA-1aB}$=J$_{5aA-5aB}$=12.8 Hz), 2.85 (dd, 2H, H1aB, H5aB, J$_{1aB-2a}$=J$_{5aB-4a}$=4.3 Hz, +compound *), 3.21 (app t, 1H, *H3a, H3a, J$_{2a-3a}$=J$_{4a-3a}$=8.3 Hz), *3.39-3.41 (2 dd, ~0.4H, *H4a, *H2a), 3.55-3.57 (2 dd, ~1.7H, H4a, H2a), 4.85 (s, CH$_2$Ph), 7.20-7.40 (m, 5H, CHar).

$^{13}$C NMR (101 MHz, CD$_3$OD): δ *51.39 (*C1a, *C5a), 51.47 (C1a, C5a), 71.92 (C2a, C4a), *72.45 (*C2a, *C4a), 75.55 (CH$_2$Ph OBn), *79.94 (*C3a), 87.12 (C3a), 127.93-128.98, 129.17 (CHar), 140.36 (Cqar).

SI-MS m/z M calculated: 223.12. found: 224.5 [M+H]$^+$, 246.5 [M+Na]$^+$.

N-trifluoroacetamido-3-O-benzyl-1,5-dideoxy-1,5-iminoxylitol (Compound 31, FIG. 2c)

SFPIM315

Pyridine (100 µl; 1.31 mmol; 1.7 eq) and trifluoroacetic anhydride (160 µl; 1.16 mmol; 1.5 eq) are added to a solution of compound 30 (172 mg; 0.77 mmol) in anhydrous dichloromethane (5 ml). The reaction medium is stirred for 18 h at ambient temperature (approximately 20° C.) and is then diluted in dichloromethane. The organic phase is washed twice with a solution of 1N HCl, and once with H$_2$O, dried over MgSO$_4$, and concentrated under vacuum. The crude product is purified by silica gel chromatography (petroleum ether/ethyl acetate 3/1.5), to give the product 31 (110 mg; 45%).

C$_{14}$H$_{15}$NO$_4$F$_3$ (M=318.28 g/mol).

$^1$H NMR (400 MHz, CDCl$_3$) δ 3.50 (d, 1H, H1A or H5A, J=13.4 Hz), 3.61 (m, 1H, H3), 3.66-3.78 (m, 3H, H1 or H5, OH), 3.82 (m, 2H, H2 or H4, OH), 3.96 (m, 1H, H4 or H2), 4.10 (dd, H1B or H5B, J=4.0, J=13.6 Hz), 4.66 (s, 2H, CH$_2$Ph), 7.25-7.38 (m, 5H, CHar).

$^{13}$C NMR (101 MHz, CDCl$_3$): δ 45.77 (C5 or C1), 48.25 and 48.28 (C1 or C5 rotamers), 67.80 (C2 or C4), 67.97 (C4 or C2), 73.04 (CH$_2$Ph), 76.52 (C3), 116.51 (q, CF$_3$, J$_{C-F}$=289 Hz), 127.78, 128.23 (3 peaks CHar), 137.71 (Car), 157.72 (q, COCF$_3$, J$_{C-F}$=36 Hz).

$^{19}$F NMR (376 MHz, CDCl$_3$): δ −67.72.

N-trifluoroacetamido-3-O-benzyl-2,4-bis-O-(2,3,4,5-tetra-O-methoxyacetyl-α-D-mannopyranosyl)-1,5-dideoxy-1,5-iminoxylitol (Compound 32, FIG. 2c)

SFPIM318

A solution of compound 17 (500 mg; 0.813 mmol; 2.5 eq) in dichloromethane (2 ml) is delivered via a cannula-like tube, under argon, into a solution of compound 31 (105 mg; 0.33 mmol) in dichloromethane (5 ml) containing 4 Å molecular sieve. The reaction mixture is stirred for 30 min at ambient temperature (approximately 20° C.) and trimethylsilyl trifluoromethanesulfonate (30 µl; 0.163 mmol; 20% relative to the imidate) is added. The reaction medium is stirred for 2 h at ambient temperature (approximately 20° C.), and then the reaction is stopped by adding triethylamine (0.8 ml) and filtered through celite. The celite is rinsed with dichloromethane, the solvent is evaporated to dryness, and the crude product is purified by silica gel chromatography (dichloromethane/acetone 6/1), to give the product 32 (188 mg; 47%) in the form of a colorless syrup.

$C_{50}H_{68}NO_{30}F_3$ (M=1220.08 g/mol).

Comment: in NMR, rotamers due to the presence of NCOCF$_3$ are observed.

$^1$H NMR (400 MHz, CDCl$_3$): δ 2.92 (dd, 0.5 H, H1aA or H5aA, J=9.9, 12.9 Hz), 3.06 (dd, 0.5 H, H1aA or H5aA, J=10.1, 12.9 Hz), 3.18 (dd, 0.5 H, H1aA or H5aA, J=9.8, 13.9 Hz), 3.26 (dd, 0.5 H, H1aA or H5aA, J=10.3, 13.9 Hz), 3.36, 3.38, 3.38, 3.40, 3.41, 3.44, 3.45, 3.48 (8 CH$_3$), 3.64-4.22 (m, 25H, 8CH$_2$ MAc, 2H5, 1H1aB or 1H5aB, 3H6, H3a, H2a, H1a), 4.40 (m, 1H, H$_6$B), 4.53 (m, 1H, H1aB or H5aB), 4.80-4.90 (m, 2H, CH2Ph), 4.94 (s, 0.5H, H1), 5.05 (s, 0.5H, H1), 5.14 (s, 0.5H, H1), 5.17 (s, 0.5H, H1), 5.24-5.45 (m, 6H, 2H2, 2H3, 2H4), 7.15-7.40 (m, 5H, CHar).

$^{13}$C NMR (101 MHz, CDCl$_3$): δ 43.44, 45.52, 45.56, 45.85, 47.89, 47.92 (6 peaks for C1a and C5a), 59.32, 59.37, 59.39, 59.41, 59.44, 59.45, 59.53 (7 CH$_3$), 61.75, 62.23, 62.58 (3 peaks for H6), 65.43, 65.56, 65.97, 66.07, 68.49, 68.62, 68.68, 68.94, 69.26, 69.49 (10 peaks for C2, C3, C4, C5), 69.14, 69.22, 69.26, 69.29, 69.39, 69.43, 69.46 (7 peaks for CH$_2$ MAc), 71.17, 72.20, 76.56, 77.08, 81.88, 82.00 (6 peaks for C1a, C2a, C3a), 75.48, 75.57 (2 peaks for CH$_2$Ph), 94.41, 94.75 (2 peaks for C1), 98.82, 99.07 (2 peaks for C1), 116.14 (q, CF$_3$, J$_{C-F}$=289 Hz), 116.21 (q, CF$_3$, J$_{C-F}$=289 Hz), 125.32-129.06 (9 peaks for CHar), 137.09, 169.12-170.18 (14 peaks for CO MAc).

$^{19}$F NMR (376 MHz, CDCl$_3$): δ -68.79, -68.55.

N-trifluoroacetamido-2,4-bis-O-(2,3,4,5-tetra-O-methoxyacetyl-α-D-mannopyranosyl)-1,5-dideoxy-1,5-iminoxylitol (Compound 33, FIG. 2c)

SFPIM319

The compound 32 (188 mg; 0.154 mmol) is dissolved in an EtOH/CH$_2$Cl$_2$ mixture (6/6 ml). An excess of palladium 10% on carbon is added and the reaction medium is stirred at ambient temperature (approximately 20° C.) under atmospheric hydrogen pressure for 3 h. The reaction medium is filtered through a millipore membrane and the catalyst is rinsed with an EtOH/CH$_2$Cl$_2$ mixture (1/1). The filtrate is evaporated under reduced pressure, so as to result in the compound 33 (168 mg; 97%).

$C_{43}H_{62}NO_{30}F_3$ (M=1129.96 g/mol).

Comment: in NMR, rotamers due to the presence of NCOCF$_3$ are observed.

$^1$H NMR (400 MHz, CDCl$_3$): δ 2.74 (app t, 0.5 H, H1aA or H5aA, J=12.1 Hz), 2.84 (app t, 0.5 H, H1aA or H5aA, J=11.6 Hz), 3.12 (m, 1H, H1aA or H5aA), 3.41, 3.42, 3.44, 3.45, 3.46, 3.47, 3.48, 3.49 (8 CH$_3$), 3.59 (m, 3H, H4a, H2a, OH), 3.74 (m, 1H, H3a), 3.88-4.49 (m, 23H, 8CH$_2$ MAc, 2H5, 1H1aB or 1H5aB, 4H6), 4.64 (m, 1H, H1aB or H5aB), 4.94 (s, 0.5H, H1), 5.01 (s, 0.5H, H1), 5.21 (s, 0.5H, H1), 5.25 (s, 0.5H, H1), 5.26-5.48 (m, 6H, 2H2, 2H3, 2H4).

$^{13}$C NMR (101 MHz, CDCl$_3$): δ 44.26, 45.61, 46.01, 47.69 (4 peaks for C1a and C5a), 59.22-59.43 (7 CH$_3$), 62.21, 62.24, 62.58 (3 peaks for H6), 65.85, 65.90, 65.98, 66.04, 68.57, 68.62, 69.07, 69.13, 69.53 (9 peaks for C2, C3, C4, C5), 69.19, 69.22, 69.33, 69.42, 69.46 (4 CH$_2$ MAc), 74.05, 74.78, 75.64, 75.84, 76.54, 77.25 (6 peaks for C1a, C2a, C3a), 95.75, 98.99 (2° C.), 116.10 (q, CF$_2$/J$_{C-F}$=289 Hz), 116.18 (q, CF$_3$, J$_{C-F}$=289 Hz), 155.58 (q, COCF$_3$, J$_{C-F}$=36 Hz), 155.62 (q, COCF$_3$, J$_{C-F}$=36 Hz), 169.16-170.18 (13 peaks COMAc).

$^{19}$F NMR (376 MHz, CDCl$_3$): δ -68.91, -68.72.

N-trifluoroacetamido-2,4-bis-O-(2,3,4,5-tetra-O-methoxyacetyl-α-D-mannopyranosyl)-(3-O-(((S)-2-O-hexadecanoyloxy-3-O-octadecanoyloxypropyl) (benzyl)-phosphoryl)-1,5-dideoxy-1,5-imino-D-xylitol (compound 34, FIG. 2c)

SFPIM322

A 0.26 M solution of the compound 22 (861 µl; 0.223 mmol; 1.5 eq) in anhydrous CH$_2$Cl$_2$ is added to a solution of compound 33 (168 mg; 0.149 mmol) in anhydrous CH$_2$Cl$_2$ (8 ml). 3 Å sieve is added and the reaction medium is stirred for 30 min at ambient temperature under argon. A commercial solution of tetrazole (~0.45 M in acetonitrile), dried beforehand on 3 Å sieve, is added at 0° C. (1.65 ml; 0.743 mmol; 5 eq) and the reaction is carried with stirring at ambient temperature for 2 h. The reaction medium is cooled to -40° C. and a solution of m-chloroperbenzoic acid (m-CPBA) (50%, 154 mg; 0.447 mmol; 3 eq) in CH$_2$Cl$_2$ (2 ml) is added dropwise. After stirring for 2 h while allowing the reaction medium to return to ambient temperature (approximately 20° C.), the reaction is stopped by adding an aqueous 50% solution of Na$_2$S$_2$O$_3$ (20 ml) and the mixture is extracted with diethyl ether (Et$_2$O) (80 ml). The organic phase is washed 4 times with an aqueous 50% solution of Na$_2$S$_2$O$_3$ (3×20 ml), once with a saturated solution of NaHCO$_2$ and once with H$_2$O, and then dried over MgSO$_4$. The solvent is evaporated off under vacuum and the residue is purified by silica gel column chromatography (4/1 toluene/acetone), to give the compound 34 (104 mg; 37%) in the form of a colorless syrup.

$C_{87}H_{139}NO_{37}F_3$ (M=1879.03 g/mol).

Comment: the spectra are difficult to interpret. This is because increased peaks owing to the rotamers linked to the presence of NCOCF$_3$, and diastereoisomers linked to the presence of the benzylated phosphate and the nonequivalence of the sugars are observed. 4 peaks can thus be noted for a sole anomeric carbon. 4 peaks are also observed in fluorine NMR.

$^{13}$C NMR (101 MHz, CDCl$_3$): δ 94.47, 94.50, 94.91, 95.00 (1C1), 98.69, 98.76, 99.18 (2C) (1C1).

$^{31}$P NMR (162 MHz, CDCl$_3$): δ -0.92.

$^{19}$F NMR (376 MHz, CDCl$_3$): δ -68.68, -68.67, -68.47, -68.44.

SI-MS m/z M calculated: 1877.87. found 1901.0 [M+Na]$^+$.

N-trifluoroacetamido-2,4-bis-O-(2,3,4,5-tetra-O-methoxyacetyl-α-D-mannopyranosyl)-(3-O-(((S)-2-O-hexadecanoyloxy-3-O-octadecanoyloxypropyl) phosphoryl)-1,5-dideoxy-1,5-imino-D-xylitol) (Compound 35, FIG. 2c)

SFPIM323

The compound 34 (90 mg; 0.048 mmol) is dissolved in an EtOH/CH$_2$Cl$_2$ mixture (6/4 ml). An excess of palladium 10% on carbon is added and the reaction medium is stirred at ambient temperature (approximately 20° C.) under atmospheric hydrogen pressure for 3 h. The reaction medium is filtered through a millipore membrane, and the catalyst is rinsed with an EtOH/CH$_2$Cl$_2$ mixture (1/1). The filtrate is evaporated under reduced pressure so as to result in the compound 35 (82 mg; 95%).

$C_{80}H_{133}NO_{37}F_3P$ (M=1788.91 g/mol).

Comment: the spectra are difficult to interpret. This is because increased peaks owing to the rotamers linked to the presence of NCOCF$_3$ and the nonequivalence of the sugars are observed. That said, the diastereoisomers have disappeared, the phosphate has been deprotected. 2 peaks for a sole anomeric carbon can also be noted. 2 peaks are also observed in fluorine NMR.

$^{13}$C NMR (101 MHz, CDCl$_3$): δ 94.54, 94.98 (1C1), 98.65, 99.17 (1C1).

$^{31}$P NMR (162 MHz, CDCl$_3$): δ −1.36, −1.30.

$^{19}$F NMR (376 MHz, CDCl$_3$): δ −68.66, −68.45.

Example 3

N-trifluoroacetamido-2,4-bis-O-(α-D-mannopyranosyl)-(3-O—(((S)-2-O-hexadecanoyloxy-3-O-octadecanoyloxypropyl)phosphoryl)-1,5-dideoxy-1,5-imino-D-xylitol (Compound 36, FIG. 2c)

SFPIM324-t2
and

Example 4

2,4-bis-O-(α-D-mannopyranosyl)-(3-O-(((S)-2-O-hexadecanoyloxy-3-O-octadecanoyloxypropyl)-phosphoryl)-1,5-dideoxy-1,5-imino-D-xylitol (Compound 37, FIG. 2c)

SFPIM324-t8

The compound 35 (80 mg; 0.045 mmol) is dissolved in a mixture of CHCl$_3$/MeOH (0.2/0.8 ml). The reaction mixture is cooled to 0° C. and t-butylamine (164 μl) is added thereto. After stirring for 10 min at 0° C. and then 1 h30 while allowing the reaction medium to return to ambient temperature (approximately 20° C.), the solvents are evaporated off under a strong vacuum at ambient temperature and the residue is purified by silica gel column chromatography (CHCl$_3$/MeOH/H$_2$O 70/40/1), to give the compound 36 (16 mg; 32%) in the first tubes and the compound 37 (21 mg; 48%) in the subsequent tubes, said compounds being in the form of white solids.

Compound 36

$C_{56}H_{101}NO_{21}PF_3$ (M=1212.39 g/mol).

Comment: the rotamers due to the presence of NCOCF$_3$ are always observed, especially at the level of the anomeric Hs.

$^1$H NMR (400 MHz, CDCl$_3$/CD$_3$OD 0.4/0.2 ml): δ 0.89 (t, 6H, 2CH3, J=6.7 Hz), 1.27 (m, 52H), 1.61 (m, 4H), 2.32 (t, 2H, J=7.6 Hz), 2.34 (t, 2H, J=7.6 Hz), 3.20-4.22 (several unresolved peaks), 4.91 (s, 0.5H, H1), 5.03 (s, 0.5H, H1), 5.12 (s, 0.5H, H1), 5.17 (s, 0.5H, H1), 5.25 (m, 1H, H2a′).

$^{31}$P NMR (162 MHz, CDCl$_3$/CD$_3$OD 0.4/0.2 ml): δ 0.161.

$^{19}$F NMR (376 MHz, CDCl$_3$/CD$_3$OD 0.4/0.2 ml): δ −68.34, −67.83.

SI-MS (−) m/z M calculated: 1211.66. found 1210.5 [M−H]$^-$.

Compound 37

$C_{54}H_{102}NO_{20}P$ (M=1116.38 g/mol)

Comment: the rotamers are no longer observed at the level of the anomeric Hs.

$^1$H NMR (250 MHz, CDCl$_3$/CD$_3$OD/D$_2$O not readily soluble): δ 0.89 (t, 6H, 2CH3, J=6.8 Hz), 1.27 (m, 52H), 1.60 (m, 4H), 2.31 (t, 2H, J=7.3 Hz), 2.34 (t, 2H, J=7.3 Hz), 3.00-4.5 (several unresolved peaks), 4.93 (s, 1H, H1), 5.08 (s, 1H, H1), 5.23 (m, 1H, H2a′).

$^{31}$P NMR (162 MHz, CDCl$_3$/CD$_3$OD/D$_2$O not readily soluble): δ 0.670.

SI-MS (−) m/z M calculated: 1115.67. found 1116.0 [M+Na]$^+$.

2) Stimulation of Wild-Type Mouse Macrophages with LPS in the Presence of Compounds 36 and 37

Figure 15:
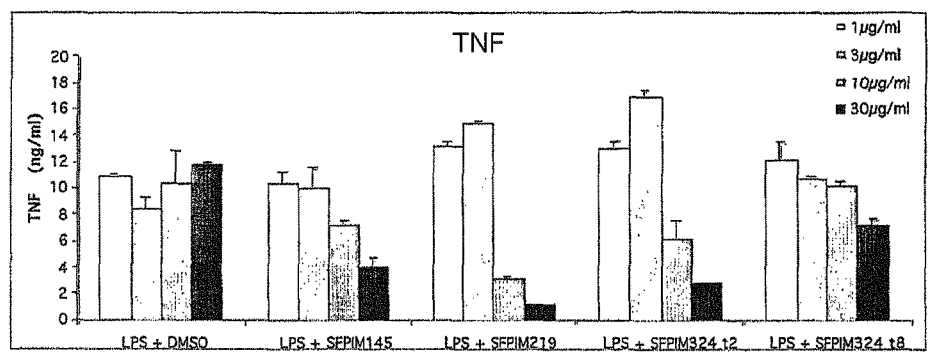
FIG. 15 represents the inhibition of TNF expression by primary macrophages stimulated with LPS in the presence of synthetic $PIM_1$ (SFPIM145), $isoPIM_1-C_{16}C_{18}$ (SFPIM219), and the compounds $PIM-2-mimNCOCF_3$ $_{(SFPIM}324$ t2) and PIM-2-mimNH(SFPIM324 t8), titrated at 1, 3, 10 and 30 µg/ml.
Figure 16:
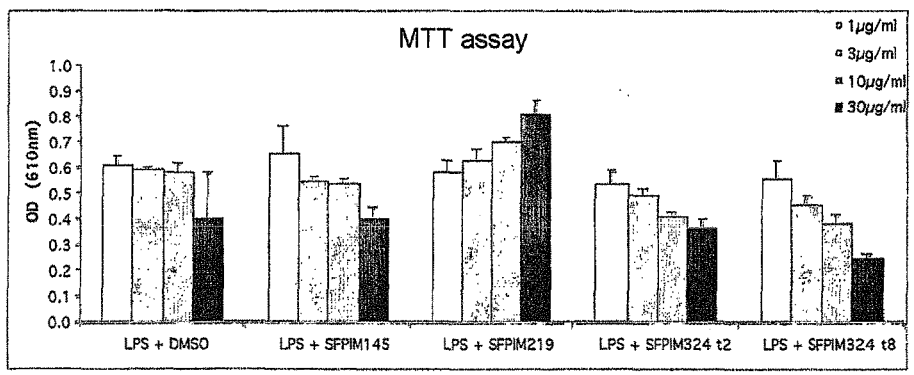
FIG. 16 represents the viability of the primary macrophages stimulated with LPS in the presence of synthetic $PIM_1$ (SFPIM145), $isoPIM_1-C_{16}C_{18}$ (SFPIM219), and the compounds PIM-2-mimNCOCF3 (SFPIM324 t2) and PIM-2-mimNH(SFPIM324 t8), titrated at 1, 3, 10 and 13 µg/ml.
Figure 17:
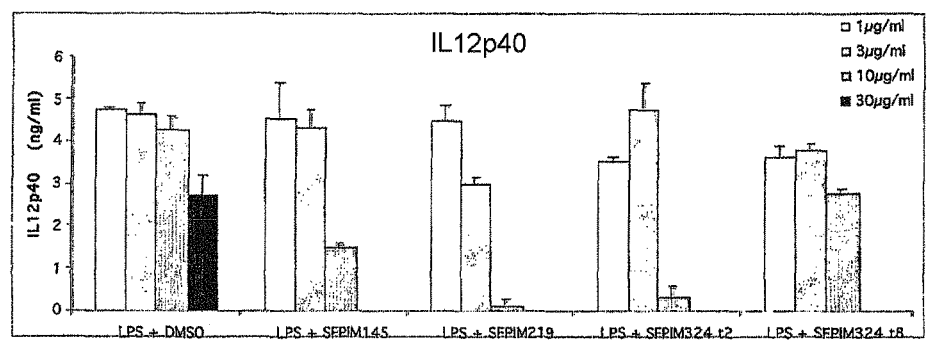
FIG. 17 represents the inhibition of IL-12 p40 expression by primary macrophages stimulated with LPS in the presence of synthetic $PIM_1$ (SFPIM145), $isoPIM_1-C_{16}C_{18}$ (SFPIM219), and the compounds $PIM-2-mimNCOCF_3$ (SFPIM324 t2) and PIM-2-mimNH(SFPIM324 t8), titrated at 1, 3, 10 and 30 µg/ml.

The compounds 36, of FIG. 2c or PIM-2-mimNCOCF$_3$ (SFPIM324 t2) and 37 of FIG. 2c or PIM-2-mimNH (SFPIM324 t8) were tested for their inhibitory activity on LPS-stimulated macrophages (FIGS. 15 to 17).

The macrophages derived from the bone marrow of wild-type mice were cultured on 96-well culture plates in a proportion of 10$^5$ cells per well, and then stimulated with LPS (100 ng/ml, *Escherichia coli*, serotype O111:B4, Sigma) with PIM$_1$ (SFPIM145), isoPIM$_1$C$_{16}$C$_{18}$ (SFPIM219) or the compounds PIM-2-mimNCOCF$_3$ (SFPIM324 t2) and PIM-2-mimNH(SFPIM324 t8) (titrated at 1, 3, 10, 30 μg/ml) or DMSO controls. The freeze-dried SFPIM145, SFPIM219, SFPIM324 t2 and SFPIM324 t8 preparations that were used are solubilized in DMSO and added to the cultures at a non-cytotoxic maximum final concentration of 1%.

After stimulation for 24 hours, the culture supernatents were collected and analyzed for their content of cytokines TNF-α or IL-12p40 by ELISA (R&D Duoset, Minneapolis, Mo.). The results correspond to the mean±SD of n=2 mice per genotype.

PIM-2-mimNCOCF$_3$ (SFPIM324 t2) and isoPIM$_1$C$_{16}$C$_{18}$ (SFPIM219) strongly inhibit TNF secretion, whereas PIM$_1$ (SFPIM145) and PIM-2-mimNH(SFPIM324 t8) inhibit less strongly (FIG. 15). An MTT cell viability assay carried out on the same macrophages indicates a certain cytotoxicity at the highest concentration, in particular in the presence of PIM-2-mimNH(SFPIM324 t8) (FIG. 16). The IL-12p40 secretion in response to LPS is virtually abolished at concentrations of 10 μg/ml of PIM-2-mimMNCOCF$_3$ (SFPIM324 t2) and of isoPIM$_1$C$_{16}$C$_{18}$ (SFPIM219), whereas PIM$_1$ (SFPIM145) and PIM-2-mimNH (SFPIM324 t8) partially inhibit at this concentration (FIG. 17).

LIST OF REFERENCES

[1] Anti-IL-12 antibodies: US2003228311 (WO 9816248); Hyaluronan: US 2004097465; IL-12 inhibitors: US 2005049262 (WO 030475); antisense RNA: US 2004241843.

[2] Keane J. (2005). TNF-blocking agents and tuberculosis: new drugs illuminate an old topic. Rheumatology (Oxford); Keane J., Gershon S., Wise R. P., Mirabile-Levens E., Kasznica J., Schwieterman W. D., Siegel J. N., and Braun, M. M. (2001), Tuberculosis associated with infliximab, a tumor necrosis factor alpha-neutralizing agent. N. Engl. J. Med. 345, 1098-1104; Mohan A. K., Cote T. R., Block J. A., Manadan A. M., Siegel J. N., and Braun M. M. (2004), Tuberculosis following the use of etanercept, a tumor necrosis factor inhibitor, Olin. Infect. Dis. 39, 295-299.

[3] Jones B. W., Means T. K., Heldwein K. A., Keen M. A., Hill P. J., Belisle J. T., and Fenton M. J. (2001), J. Leukoc. Biol. 69, 1036-1044.

[4] Sieling P. A., Chatterjee D., Porcelli S. A., Prigozy T. I., Mazzaccaro R. J., Soriano T., Bloom B. R., Brenner M. B., Kronenberg M., Brennan P. J. (1995) Science 269, 227-230.

[5] Ernst W. A., Maher J., Cho S., Niazi K. R., Chatterjee D., Moody D. B., Besra G. S., Watanabe Y., Jensen P. E., Porcelli S. A., Kronenberg M., and Modlin R. L. (1998) Immunity 8, 331-340.

[6] Apostolou I., Takahama Y., Belmant C., Kawano T., Huerre M., Marchal G., Cui J., Taniguchi M., Nakauchi H., Fournie J. J., Kourilsky P., Gachelin G. (1999) Proc. Natl. Acad. Sci. USA 96, 5141-5146.

[7] Gilleron, M., Ronet, C., Mempel, M., Monsarrat, B., Gachelin, G., and Puzo, G. (2001) J Biol Chem 276, 34896-34904.

[8] Knutson, K. L., Z. Hmama, P. Herrera-Velit, R. Rochford, and N. E. Reiner. 1998. Lipoarabinomannan of *Mycobacterium tuberculosis* promotes protein tyrosine dephosphorylation and inhibition of mitogen-activated protein kinase in human mononuclear phagocytes. Role of the Src homology 2 containing tyrosine phosphatase 1. J Biol Chem 273:645; Nigou, J., Zelle-Rieser, C., Gilleron, M., Thurnher, M., and Puzo, G. (2001) J Immunol 166, 7477-7485; Geijtenbeek, T. B., S. J. Van Vliet, E. A. Koppel, M. Sanchez-Hernandez, C. M. Vandenbroucke-Grauls, B. Appelmelk, and Y. Van Kooyk. 2003, *Mycobacteria* target DC-SIGN to suppress dendritic cell function. J Exp Med 197:7.

[9] Means T K, Wang S, Yoshimura A, Golenbock D T and Fenton M J. Human Toll-like receptors mediate cellular activation by *Mycobacterium tuberculosis*. J Immunol 163: 3920-3927 (1999).

[10] Nigou, J., Zelle-Rieser, C., Gilleron, M., Thurnher, M., and Puzo, G. (2001) J Immunol 166, 7477-7485.

[11] Maeda, N., J. Nigou, J. L. Herrmann, M. Jackson, A. Amara, P. H. Lagrange, G. Puzo, B. Gicquel, and O. Neyrolles, 2003, The cell surface receptor DC-SIGN discriminates between *Mycobacterium* species through selective recognition of the mannose caps on lipoarabinomannan, J Biol Chem 278:5513; Geijtenbeek, T. B., S. J. Van Vliet, E. A. Koppel, M. Sanchez-Hernandez, C. M. Vandenbroucke-Grauls, B. Appelmelk, and Y. Van Kooyk. 2003.

[12] Besra, G. S., C. B. Morehouse, C. M. Rittner, C. J. Waechter, and P. J. Brennan. 1997. Biosynthesis of mycobacterial lipoarabinomannan. J Biol Chem 272:18460; Nigou, J., M. Gilleron, and G. Puzo. 2003. Lipoarabinomannans: from structure to biosynthesis, Biochimie 85:153.

[13] Quesniaux, V. J., Nicolle, D. M., Torres, D., Kremer, L., Guerardel, Y., Nigou, J., Puzo, G., Erard, F., and Ryffel, B. (2004). Toll-like receptor 2 (TLR2)-dependent-positive and TLR2-independent-negative regulation of proinflammatory cytokines by mycobacterial lipomannans. J Immunol 172, 4425-4434.

[14] Gilleron M, Nigou J, Nicolle D, Quesniaux V and Puzo G. The acylation state of mycobacterial lipomannans modulates innate immunity response through Toll-like receptor 2. Chem Biol 13:39-47 (2006); Doz E., Rose S., Nigou J., Gilleron M., Puzo G., Erard F., Ryffel B. and Quesniaux V. F. J. (2007) Acylation determines the TLR-dependent positive versus mannose receptor- and SIGNR1-independent negative regulation of proinflammatory cytokines by mycobacterial lipomannan. J. Biol. Chem. 282:26014-25.

[15] Doz E., Rose S., Nigou J., Gilleron M., Puzo G., Erard F., Ryffel B. and Quesniaux V. F. J. (2007) Acylation determines the TLR-dependent positive versus mannose receptor- and SIGNR1-independent negative regulation of proinflammatory cytokines by mycobacterial lipomannan. J. Biol. Chem. 282:26014-25.

[16] Kordulakova, J., Gilleron, M., Mikusova, K., Puzo, G., Brennan, P. J., Gicquel, B., and Jackson, M. (2002) J Biol. Chem.

[17] Schaeffer, M. L., Khoo, K. H., Besra, G. S., Chatterjee, D., Brennan, P. J., Belisle, J. T., and Inamine, J. M. (1999) J Biol Chem 274, 31625-31631.

[18] Kremer, L., Gurcha, S. S., Bifani, P., Hitchen, P. G., Baulard, A., Morris, H. R., Dell, A., Brennan, P. J., and Besra, G. S. (2002) Biochem J 363, 437-447.

[19] Gilleron, M., Quesniaux, V. F., and Puzo, G. (2003). Acylation state of the phosphatidyl inositol hexamannosides from *mycobacterium bovis* BCG and *mycobacterium tuberculosis* H37Rv and its implication in TLR response. J Biol Chem 278, 29880-29889.

[20] Stadelmaier A, Schmidt R R. (2003) Synthesis of phosphatidylinositol mannosides (PIMs). Carbohydr Res. 338: 2557-69; Liu X, Stocker B L, Seeberger P H. (2006) Total synthesis of phosphatidylinositol mannosides of *Mycobacterium tuberculosis*. J Am Chem. Soc. 128:3638-48.

[21] Figueroa-Perez, I., Stadelmaier, A., Morath, S., Hartung, T., Schmidt, Richard R. (2005) Synthesis of structural variants of *Staphylococcus aureus* lipoteichoic acid (LTA) Tetrahedron Asymmetry 16, 493-506; Dyer, B. S., Jones, J. D., Ainge, G. D., Denis, M., Larsen, D. S, and Painter, G. F. (2007). Synthesis and structure of phosphatidylinositol Dimmanoside. J. Org. Chem. 72, 3282-3288.

[22] Muller, M., Eugster, H. P., Le Hir, M., Shakhov, A., Di Padova, F., Maurer, C., Quesniaux, V. F., and Ryffel, B. (1996) Mol Med 2, 247-255.

[23] Togbe D., Moulin N., Grivennikov S I., Couillin I, Maillet I, Jacobs M, Maret M, Fick L, Nedospasov S A, Quesniaux V F J, Schnyder B and Schnyder-Candrian S. (2007) T cell derived TNF downregulates acute airway response to endotoxin Eur. J. Immunol. 37:768-79.

[24] Lindberg et al. *Tetrahedron,* 2002, 58, 1387-1398.

[25] Miculka C. (1999), Synlett, 948-950.

The invention claimed is:

1. A compound of general formula (I):

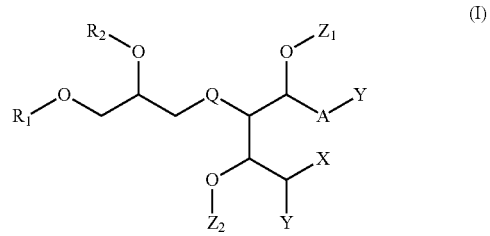

in which:

$R_1$ and $R_2$ represent, independently of one another, a hydrogen atom, a $C_1$-$C_{20}$ alkyl radical or a $C_1$-$C_{20}$ acyl radical, it being understood that, when one of the substituents $R_1$ or $R_2$ is a hydrogen atom, the other substituent is other than hydrogen;

$Z_1$ and $Z_2$ represent, independently of one another, a hydrogen atom, or at least one sugar chosen from the group comprising mannose, glucose and galactose, it being understood that, when one of the substituents $Z_1$ or $Z_2$ is a hydrogen atom, the other substituent is other than hydrogen;

Q represents —OP(O)$_2$O—, —OCO$_2$—, —NHCO$_2$— or —NHCONH—;

Y represents a hydrogen atom, a hydroxyl radical, a $C_1$-$C_6$ alkoxy radical, or —(CH$_2$)$_n$—OH, with n being an integer equal to 1, 2 or 3, it being understood that, when Y is a hydroxyl radical, $Z_1$ and $Z_2$ do not both represent a hydrogen atom;

A represents —CH$_2$—;

X represents a hydrogen atom;

or A and X together form a bond so as to result in a 6-membered ring in which:

A represents a —CH—,

X represents a —CH$_2$—, —CH(OH)—, an oxygen atom, an —NR$_3$— in which R$_3$ is a hydrogen atom, a $C_1$-$C_6$ alkyl radical or a $C_1$-$C_{20}$ acyl radical, it being understood that, when A and X form a bond so as to result in a 6-membered ring,
X=—CH(OH)—,
Y=—OH, and
$Z_1$ and $Z_2$ represent, independently of one another, at least one sugar chosen from the group comprising mannose, glucose and galactose, the 6-membered ring is in the myo-inositol configuration with $Z_1$ or $Z_2$ in position 1 and representing at least one sugar;
or a pharmaceutically acceptable salt thereof.

2. The compound as claimed in claim 1, in which A and X together form a bond so as to result in a 6-membered ring, of formula (Ia)

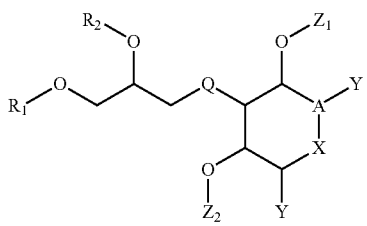

(Ia)

in which:
is $R_1$ and $R_2$, $Z_1$ and $Z_2$, Q and Y are as defined in claim 1;
A represents a —CH—;
X represents a —CH$_2$—, —CH(OH)—, an oxygen atom, an —NR$_3$— in which $R_3$ is a hydrogen atom, a $C_1$-$C_6$ alkyl radical or a $C_1$-$C_{20}$ acyl radical,
it being understood that, when
X=—CH(OH)—,
Y=—OH, and
$Z_1$ and $Z_2$ represent, independently of one another, at least one sugar chosen from the group comprising mannose, glucose and galactose,
the 6-membered ring is in the myo-inositol configuration with $Z_1$ or $Z_2$ in position 1 and representing at least one sugar;
or a pharmaceutically acceptable salt thereof.

3. The compound as claimed in either of claims 1 or 2, in which A and X together form a bond so as to result in a 6-membered ring, in which:
$R_1$ and $R_2$ are as defined in claim 1;
Q represents —OP(O)$_2$O—;
A represents a —CH—;
X represents —CH(OH)—
Y represents a hydroxyl radical;
$Z_1$ and $Z_2$ represent, independently of one another, at least one sugar chosen from the group comprising mannose, glucose and galactose,
the 6-membered ring is in the myo-inositol configuration with $Z_1$ or $Z_2$ in position 1 and representing at least one sugar;
or a pharmaceutically acceptable salt thereof.

4. The compound as claimed in either of claims 1 or 2, in which A and X together form a bond so as to result in a 6-membered ring, in which:
$R_1$ and $R_2$, $Z_1$ and $Z_2$ and Y are as defined in claim 1;
Q represents —OP(O)$_2$O—;
A represents a —CH—;
X represents an —NR$_3$— in which $R_3$ is a hydrogen atom, a $C_1$-$C_6$ alkyl radical or a $C_1$-$C_{20}$ acyl radical;
or a pharmaceutically acceptable salt thereof.

5. The compound as claimed in claim 1, of formula (Ib)

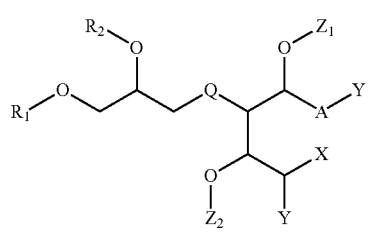

(Ib)

in which:
$R_1$ and $R_2$, $Z_1$ and $Z_2$, Q and Y are as defined in claim 1;
A represents —CH$_2$—;
X represents a hydrogen atom;
or a pharmaceutically acceptable salt thereof.

6. The compound as claimed in either of claims 1 or 2, in which A and X together form a bond so as to result in a 6-membered ring, in which:
$R_1$ and $R_2$ represent, independently of one another, a $C_1$-$C_{20}$ acyl radical;
$Z_1$ represents mannose;
$Z_2$ represents a hydrogen atom;
Q represents —OP(O)$_2$O—;
A represents a —CH—;
X represents a —CH(OH)—;
Y represents a hydroxyl radical;
the 6-membered ring is in the myo-inositol configuration with $Z_1$ in position 1;
or a pharmaceutically acceptable salt thereof.

7. A pharmaceutical composition comprising at least one compound as defined in claim 1 and any pharmaceutically acceptable excipient.

* * * * *